(12) United States Patent
Lin et al.

(10) Patent No.: US 7,695,941 B2
(45) Date of Patent: Apr. 13, 2010

(54) MULTIPLEXED POLYMERASE CHAIN REACTION FOR GENETIC SEQUENCE ANALYSIS

(75) Inventors: Baochuan Lin, Bethesda, MD (US); Kate M. Blaney, Alexandria, VA (US); Anthony P. Malanoski, Greenbelt, MD (US); Joel M Schnur, Burke, VA (US); David A Stenger, Herndon, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 11/422,425

(22) Filed: Jun. 6, 2006

(65) Prior Publication Data

US 2006/0286580 A1    Dec. 21, 2006

Related U.S. Application Data

(63) Continuation-in-part of application No. 11/177,647, filed on Jul. 2, 2005, and a continuation-in-part of application No. 11/177,646, filed on Jul. 2, 2005, and a continuation-in-part of application No. 11/268,373, filed on Nov. 7, 2005.

(60) Provisional application No. 60/691,768, filed on Jun. 16, 2005, provisional application No. 60/735,876, filed on Nov. 14, 2005, provisional application No. 60/735,824, filed on Nov. 14, 2005, provisional application No. 60/743,639, filed on Mar. 22, 2006.

(51) Int. Cl.
*C12Q 1/68* (2006.01)
*C12P 19/34* (2006.01)

(52) U.S. Cl. .......................... 435/91.2; 435/6; 435/91.1

(58) Field of Classification Search ........................ None
See application file for complete search history.

(56) References Cited

U.S. PATENT DOCUMENTS

| | | | |
|---|---|---|---|
| 5,314,809 A | | 5/1994 | Erlich et al. |
| 5,837,832 A | * | 11/1998 | Chee et al. ................. 536/22.1 |
| 5,853,989 A | * | 12/1998 | Jeffreys et al. ................ 435/6 |
| 5,958,686 A | * | 9/1999 | Houng ........................... 435/6 |
| 6,258,570 B1 | * | 7/2001 | Glustein et al. ............ 435/91.2 |
| 6,270,967 B1 | * | 8/2001 | Whitcombe et al. ............ 435/6 |
| 6,287,776 B1 | * | 9/2001 | Hefti ............................... 435/6 |
| 6,843,997 B2 | * | 1/2005 | Grose et al. .............. 424/230.1 |
| 2002/0031777 A1 | | 3/2002 | Starr-Spires |
| 2003/0082618 A1 | * | 5/2003 | Li et al. .......................... 435/6 |
| 2003/0124512 A1 | * | 7/2003 | Stuyver ......................... 435/5 |

OTHER PUBLICATIONS

Zhang et al., "A multiplex PCR for identifying Shiga-like toxin-producing *Escherichia coli* O157:H7," Letters in Applied Microbiology, 1997, vol. 24, pp. 172-176.*

Lindblad-Toh et al., "Large-scale discovery and genotyping of single-nucleotide polymorphisms in the mouse," Nature Genetics, Apr. 2000, vol. 24, pp. 381-386.*

Kulski et al., "Use of a Multiplex PCR to Detect and Identify Mycobacterium avium and M. intracellulare in Blood Culture Fluids of AIDS Patients," Journal of Clinical Microbiology, Mar. 1995, vol. 33, No. 3, pp. 668-674.*

Candotti et al., "Multiplex real-time quantitative RT-PCR assay for hepatitis B virus, hepatitis C virus, and human immunodeficiency virus type 1," Journal of Virological Methods, 2004, vol. 118, pp. 39-47.*

Huang et al., "Multiplex PCR for rapid detection of pseudorabies virus, porcine parvovirus and porcine circoviruses," Veterinary Microbiology, 2004, vol. 101, pp. 209-214.*

Brownie et al., "The elimination of primer-dimer accumulation in PCR" *Nucleic Acids Res.*, 25, 3235-3241 (1997).

Call et al., "Mixed-genome microarrays reveal multiple serotype and lineage-specific differences among strains of *Listeria monocytogenes*" *J. Clin. Microbiol.*, 41, 632-639 (2003).

Call et al., "Identifying antimicrobial resistance genes with DNA microarrays" *Antimicrob. Agents Chemother.*, 47, 3290-3295 (2003).

Chizhikov et al., "Microarray analysis of microbial virulence factors" *Appl. Environ. Microbiol.*, 67, 3258-3263 (2001).

Chizhikov et al., "Detection and genotyping of human group A rotaviruses by oligonucleotide microarray hybridization" *J. Clin. Microbiol.*, 40, 2398-2407 (2002).

Lin et al., "Broad-spectrum respiratory tract pathogen identification using resequencing DNA microarrays" *Genome Res.*, 16(4), 527-535 (2006).

Shuber et al., "A simplified procedure for developing multiplex PCRs" *Genome Res.*, 5, 488-493 (1995).

Vora et al., "Microarray-based detection of genetic heterogeneity, antimicrobial resistance, and the viable but nonculturable state in human pathogenic *Vibrio* ssp.," *PNAS*, 102(52), 19109-19114 (2005).

Wang et al., "Identifying Influenza Viruses with Resequencing Microarrays" *Emerg. Infect. Dis.*, 12(4), 638-646 (2006).

Wilson et al., "Sequence-specific identification of 18 pathogenic microorganisms using microarray technology" *Mol. Cell. Probes*, 16, 119-127 (2002).

Wilson et al., "High-density microarray of small-subunit ribosomal DNA probes" *Appl. Environ. Microbiol.*, 68, 2535-2541(2002).

Written Opinion in SG 200718669-5.
Examination report in NZ564991.
CIPO Communication in CA2612412.

* cited by examiner

*Primary Examiner*—Young J Kim
(74) *Attorney, Agent, or Firm*—John J. Karasek; Joseph T. Grunkemeyer

(57) ABSTRACT

A PCR method involving: providing a biological sample suspected of containing one or more pathogen nucleic acids; adding a plurality of PCR primers corresponding to genes found in the pathogens; and performing a polymerase chain reaction on the sample to amplify a subset of the nucleic acids that correspond to the genes. The primers include at least one primer pair for each pathogen, and the primers contain a tail sequence that is not homologous any pathogen DNA or to any background DNA in the sample. The concentration of at least one primer in the polymerase chain reaction is no more than about 100 nM.

24 Claims, No Drawings

```
                           SEQUENCE LISTING

<160> NUMBER OF SEQ ID NOS: 147

<210> SEQ ID NO 1
<211> LENGTH: 22
<212> TYPE: DNA
<213> ORGANISM: Artificial
<220> FEATURE:
<223> OTHER INFORMATION: Primer tail sequence

<400> SEQUENCE: 1
cgatacgacg ggcgtactag cg                                              22

<210> SEQ ID NO 2
<211> LENGTH: 31
<212> TYPE: DNA
<213> ORGANISM: Artificial
<220> FEATURE:
<223> OTHER INFORMATION: Primer tail sequence
<220> FEATURE:
<221> NAME/KEY: misc_feature
<222> LOCATION: (23)..(31)
<223> OTHER INFORMATION: n is a, t, c, or g

<400> SEQUENCE: 2
cgatacgacg ggcgtactag cgnnnnnnnn n                                    31

<210> SEQ ID NO 3
<211> LENGTH: 42
<212> TYPE: DNA
<213> ORGANISM: Artificial
<220> FEATURE:
<223> OTHER INFORMATION: Primer

<400> SEQUENCE: 3
cgatacgacg ggcgtactag cggccaacaa ctcaaccgac ac                        42

<210> SEQ ID NO 4
<211> LENGTH: 44
<212> TYPE: DNA
<213> ORGANISM: Artificial
<220> FEATURE:
<223> OTHER INFORMATION: Primer

<400> SEQUENCE: 4
cgatacgacg ggcgtactag cgacacttcg catcacattc atcc                      44

<210> SEQ ID NO 5
<211> LENGTH: 42
<212> TYPE: DNA
<213> ORGANISM: Artificial
<220> FEATURE:
```

-continued

<223> OTHER INFORMATION: Primer

<400> SEQUENCE: 5
cgatacgacg ggcgtactag cgacttcccg gaaatgacaa ca            42

<210> SEQ ID NO 6
<211> LENGTH: 42
<212> TYPE: DNA
<213> ORGANISM: Artificial
<220> FEATURE:
<223> OTHER INFORMATION: Primer

<400> SEQUENCE: 6
cgatacgacg ggcgtactag cgggtttgtc attgggaatg ct            42

<210> SEQ ID NO 7
<211> LENGTH: 42
<212> TYPE: DNA
<213> ORGANISM: Artificial
<220> FEATURE:
<223> OTHER INFORMATION: Primer

<400> SEQUENCE: 7
cgatacgacg ggcgtactag cggccattcc acaacataca cc            42

<210> SEQ ID NO 8
<211> LENGTH: 42
<212> TYPE: DNA
<213> ORGANISM: Artificial
<220> FEATURE:
<223> OTHER INFORMATION: Primer

<400> SEQUENCE: 8
cgatacgacg ggcgtactag cgagctacca tgattgccag tg            42

<210> SEQ ID NO 9
<211> LENGTH: 42
<212> TYPE: DNA
<213> ORGANISM: Artificial
<220> FEATURE:
<223> OTHER INFORMATION: primer

<400> SEQUENCE: 9
cgatacgacg ggcgtactag cgacgttgtt gctggaaagg ac            42

<210> SEQ ID NO 10
<211> LENGTH: 42
<212> TYPE: DNA
<213> ORGANISM: Artificial
<220> FEATURE:
<223> OTHER INFORMATION: primer

<400> SEQUENCE: 10
cgatacgacg ggcgtactag cgaaacttcc gctgtaccct ga            42

<210> SEQ ID NO 11
<211> LENGTH: 43
<212> TYPE: DNA
<213> ORGANISM: Artificial
<220> FEATURE:
<223> OTHER INFORMATION: primer

<400> SEQUENCE: 11
cgatacgacg ggcgtactag cgggaaatat gccccaaact agc           43

```
<210> SEQ ID NO 12
<211> LENGTH: 42
<212> TYPE: DNA
<213> ORGANISM: Artificial
<220> FEATURE:
<223> OTHER INFORMATION: primer

<400> SEQUENCE: 12
cgatacgacg ggcgtactag cgatgcagct tttgccttca ac                    42

<210> SEQ ID NO 13
<211> LENGTH: 42
<212> TYPE: DNA
<213> ORGANISM: Artificial
<220> FEATURE:
<223> OTHER INFORMATION: primer

<400> SEQUENCE: 13
cgatacgacg ggcgtactag cgttctaacc gaggtcgaaa cg                    42

<210> SEQ ID NO 14
<211> LENGTH: 42
<212> TYPE: DNA
<213> ORGANISM: Artificial
<220> FEATURE:
<223> OTHER INFORMATION: primer

<400> SEQUENCE: 14
cgatacgacg ggcgtactag cgctctggca ctccttccgt ag                    42

<210> SEQ ID NO 15
<211> LENGTH: 42
<212> TYPE: DNA
<213> ORGANISM: Artificial
<220> FEATURE:
<223> OTHER INFORMATION: primer

<400> SEQUENCE: 15
cgatacgacg ggcgtactag cggggaggtc aatgtgactg gt                    42

<210> SEQ ID NO 16
<211> LENGTH: 42
<212> TYPE: DNA
<213> ORGANISM: Artificial
<220> FEATURE:
<223> OTHER INFORMATION: primer

<400> SEQUENCE: 16
cgatacgacg ggcgtactag cggggcaatt tcctatggct tt                    42

<210> SEQ ID NO 17
<211> LENGTH: 42
<212> TYPE: DNA
<213> ORGANISM: Artificial
<220> FEATURE:
<223> OTHER INFORMATION: primer

<400> SEQUENCE: 17
cgatacgacg ggcgtactag cggtgaaccg ttctgcaaca aa                    42

<210> SEQ ID NO 18
<211> LENGTH: 42
<212> TYPE: DNA
<213> ORGANISM: Artificial
<220> FEATURE:
<223> OTHER INFORMATION: primer
```

```
<400> SEQUENCE: 18
cgatacgacg ggcgtactag cgccaatctt ggatgccatt ct                    42

<210> SEQ ID NO 19
<211> LENGTH: 44
<212> TYPE: DNA
<213> ORGANISM: Artificial
<220> FEATURE:
<223> OTHER INFORMATION: primer

<400> SEQUENCE: 19
cgatacgacg ggcgtactag cgcattgaca gaagatggag aagg                  44

<210> SEQ ID NO 20
<211> LENGTH: 41
<212> TYPE: DNA
<213> ORGANISM: Artificial
<220> FEATURE:
<223> OTHER INFORMATION: primer

<400> SEQUENCE: 20
cgatacgacg ggcgtactag cgaagcacag agcgttccta g                     41

<210> SEQ ID NO 21
<211> LENGTH: 42
<212> TYPE: DNA
<213> ORGANISM: Artificial
<220> FEATURE:
<223> OTHER INFORMATION: primer

<400> SEQUENCE: 21
cgatacgacg ggcgtactag cgctgtggac cgtgaggata ct                    42

<210> SEQ ID NO 22
<211> LENGTH: 43
<212> TYPE: DNA
<213> ORGANISM: Artificial
<220> FEATURE:
<223> OTHER INFORMATION: primer

<400> SEQUENCE: 22
cgatacgacg ggcgtactag cgttggcggg tatagggtag agc                   43

<210> SEQ ID NO 23
<211> LENGTH: 43
<212> TYPE: DNA
<213> ORGANISM: Artificial
<220> FEATURE:
<223> OTHER INFORMATION: primer

<400> SEQUENCE: 23
cgatacgacg ggcgtactag cgttattcag cagcacctcc ttg                   43

<210> SEQ ID NO 24
<211> LENGTH: 42
<212> TYPE: DNA
<213> ORGANISM: Artificial
<220> FEATURE:
<223> OTHER INFORMATION: primer

<400> SEQUENCE: 24
cgatacgacg ggcgtactag cgggtggcag gttgaatact ag                    42

<210> SEQ ID NO 25
<211> LENGTH: 43
```

```
<212> TYPE: DNA
<213> ORGANISM: Artificial
<220> FEATURE:
<223> OTHER INFORMATION: primer

<400> SEQUENCE: 25
cgatacgacg ggcgtactag cgggctgata atcttccacc tcc       43

<210> SEQ ID NO 26
<211> LENGTH: 43
<212> TYPE: DNA
<213> ORGANISM: Artificial
<220> FEATURE:
<223> OTHER INFORMATION: primer

<400> SEQUENCE: 26
cgatacgacg ggcgtactag cgctctcacg gcaactggtt taa       43

<210> SEQ ID NO 27
<211> LENGTH: 42
<212> TYPE: DNA
<213> ORGANISM: Artificial
<220> FEATURE:
<223> OTHER INFORMATION: primer

<400> SEQUENCE: 27
cgatacgacg ggcgtactag cggacaggac gcttcggagt ac        42

<210> SEQ ID NO 28
<211> LENGTH: 44
<212> TYPE: DNA
<213> ORGANISM: Artificial
<220> FEATURE:
<223> OTHER INFORMATION: primer

<400> SEQUENCE: 28
cgatacgacg ggcgtactag cgggcaacat tggcatagag gaag      44

<210> SEQ ID NO 29
<211> LENGTH: 40
<212> TYPE: DNA
<213> ORGANISM: Artificial
<220> FEATURE:
<223> OTHER INFORMATION: primer

<400> SEQUENCE: 29
cgatacgacg ggcgtactag cgggtggagt gatggcttcg           40

<210> SEQ ID NO 30
<211> LENGTH: 43
<212> TYPE: DNA
<213> ORGANISM: Artificial
<220> FEATURE:
<223> OTHER INFORMATION: primer

<400> SEQUENCE: 30
cgatacgacg ggcgtactag cgagtgccat ctatgctatc tcc       43

<210> SEQ ID NO 31
<211> LENGTH: 42
<212> TYPE: DNA
<213> ORGANISM: Artificial
<220> FEATURE:
<223> OTHER INFORMATION: primer

<400> SEQUENCE: 31
```
cgatacgacg ggcgtactag cggccgtgga gtaaatggct aa         42

```
<210> SEQ ID NO 32
<211> LENGTH: 42
<212> TYPE: DNA
<213> ORGANISM: Artificial
<220> FEATURE:
<223> OTHER INFORMATION: primer

<400> SEQUENCE: 32
```
cgatacgacg ggcgtactag cgagtcttcc aagaccgtcc aa         42

```
<210> SEQ ID NO 33
<211> LENGTH: 41
<212> TYPE: DNA
<213> ORGANISM: Artificial
<220> FEATURE:
<223> OTHER INFORMATION: primer

<400> SEQUENCE: 33
```
cgatacgacg ggcgtactag cgatgtgacc accgaccgta g          41

```
<210> SEQ ID NO 34
<211> LENGTH: 41
<212> TYPE: DNA
<213> ORGANISM: Artificial
<220> FEATURE:
<223> OTHER INFORMATION: primer

<400> SEQUENCE: 34
```
cgatacgacg ggcgtactag cggttgctgg agaacggtat g          41

```
<210> SEQ ID NO 35
<211> LENGTH: 45
<212> TYPE: DNA
<213> ORGANISM: Artificial
<220> FEATURE:
<223> OTHER INFORMATION: primer

<400> SEQUENCE: 35
```
cgatacgacg ggcgtactag cgtctacccc tatgaagatg aaagc      45

```
<210> SEQ ID NO 36
<211> LENGTH: 45
<212> TYPE: DNA
<213> ORGANISM: Artificial
<220> FEATURE:
<223> OTHER INFORMATION: primer

<400> SEQUENCE: 36
```
cgatacgacg ggcgtactag cgggataggc agttgtgctg ggcat      45

```
<210> SEQ ID NO 37
<211> LENGTH: 41
<212> TYPE: DNA
<213> ORGANISM: Artificial
<220> FEATURE:
<223> OTHER INFORMATION: primer

<400> SEQUENCE: 37
```
cgatacgacg ggcgtactag cgtgagtgcc agcgagaaga g          41

```
<210> SEQ ID NO 38
<211> LENGTH: 44
<212> TYPE: DNA
<213> ORGANISM: Artificial
```

<220> FEATURE:
<223> OTHER INFORMATION: primer

<400> SEQUENCE: 38
cgatacgacg ggcgtactag cgcaggaggt gaggtagttg aatc            44

<210> SEQ ID NO 39
<211> LENGTH: 42
<212> TYPE: DNA
<213> ORGANISM: Artificial
<220> FEATURE:
<223> OTHER INFORMATION: primer

<400> SEQUENCE: 39
cgatacgacg ggcgtactag cgtcaaatcc tcgttgacag ac            42

<210> SEQ ID NO 40
<211> LENGTH: 42
<212> TYPE: DNA
<213> ORGANISM: Artificial
<220> FEATURE:
<223> OTHER INFORMATION: primer

<400> SEQUENCE: 40
cgatacgacg ggcgtactag cgtgcactgt tgcctccatt ga            42

<210> SEQ ID NO 41
<211> LENGTH: 43
<212> TYPE: DNA
<213> ORGANISM: Artificial
<220> FEATURE:
<223> OTHER INFORMATION: primer

<400> SEQUENCE: 41
cgatacgacg ggcgtactag cgacaggaat tggctcagat atg           43

<210> SEQ ID NO 42
<211> LENGTH: 42
<212> TYPE: DNA
<213> ORGANISM: Artificial
<220> FEATURE:
<223> OTHER INFORMATION: primer

<400> SEQUENCE: 42
cgatacgacg ggcgtactag cgacatgatc tcctgttgtc gt            42

<210> SEQ ID NO 43
<211> LENGTH: 43
<212> TYPE: DNA
<213> ORGANISM: Artificial
<220> FEATURE:
<223> OTHER INFORMATION: primer

<400> SEQUENCE: 43
cgatacgacg ggcgtactag cgtcgaggtt gccaggatat agg           43

<210> SEQ ID NO 44
<211> LENGTH: 44
<212> TYPE: DNA
<213> ORGANISM: Artificial
<220> FEATURE:
<223> OTHER INFORMATION: primer

<400> SEQUENCE: 44
cgatacgacg ggcgtactag cgggactatg agatgcctga ttgc          44

<210> SEQ ID NO 45
<211> LENGTH: 44
<212> TYPE: DNA
<213> ORGANISM: Artificial
<220> FEATURE:
<223> OTHER INFORMATION: primer

<400> SEQUENCE: 45
cgatacgacg ggcgtactag cgcaactatt agcagtcaca ctcg                           44

<210> SEQ ID NO 46
<211> LENGTH: 43
<212> TYPE: DNA
<213> ORGANISM: Artificial
<220> FEATURE:
<223> OTHER INFORMATION: primer

<400> SEQUENCE: 46
cgatacgacg ggcgtactag cgaagttggc attgtgttca gtg                            43

<210> SEQ ID NO 47
<211> LENGTH: 41
<212> TYPE: DNA
<213> ORGANISM: Artificial
<220> FEATURE:
<223> OTHER INFORMATION: primer

<400> SEQUENCE: 47
cgatacgacg ggcgtactag cgtcatccag actgtcaaag g                              41

<210> SEQ ID NO 48
<211> LENGTH: 42
<212> TYPE: DNA
<213> ORGANISM: Artificial
<220> FEATURE:
<223> OTHER INFORMATION: primer

<400> SEQUENCE: 48
cgatacgacg ggcgtactag cgaaacagga aacacggaca cc                             42

<210> SEQ ID NO 49
<211> LENGTH: 44
<212> TYPE: DNA
<213> ORGANISM: Artificial
<220> FEATURE:
<223> OTHER INFORMATION: primer

<400> SEQUENCE: 49
cgatacgacg ggcgtactag cgctctatca tcacagatct cagc                           44

<210> SEQ ID NO 50
<211> LENGTH: 42
<212> TYPE: DNA
<213> ORGANISM: Artificial
<220> FEATURE:
<223> OTHER INFORMATION: primer

<400> SEQUENCE: 50
cgatacgacg ggcgtactag cgatgagtc tgactggttt gc                              42

<210> SEQ ID NO 51
<211> LENGTH: 44
<212> TYPE: DNA
<213> ORGANISM: Artificial
<220> FEATURE:
<223> OTHER INFORMATION: primer

<400> SEQUENCE: 51
cgatacgacg ggcgtactag cgacaaagat ggctcttagc aaag        44

<210> SEQ ID NO 52
<211> LENGTH: 44
<212> TYPE: DNA
<213> ORGANISM: Artificial
<220> FEATURE:
<223> OTHER INFORMATION: primer

<400> SEQUENCE: 52
cgatacgacg ggcgtactag cgacccagtg aatttatgat tagc        44

<210> SEQ ID NO 53
<211> LENGTH: 42
<212> TYPE: DNA
<213> ORGANISM: Artificial
<220> FEATURE:
<223> OTHER INFORMATION: primer

<400> SEQUENCE: 53
cgatacgacg ggcgtactag cgaaaaccaa cccaaccaaa cc          42

<210> SEQ ID NO 54
<211> LENGTH: 44
<212> TYPE: DNA
<213> ORGANISM: Artificial
<220> FEATURE:
<223> OTHER INFORMATION: primer

<400> SEQUENCE: 54
cgatacgacg ggcgtactag cggcacatca taattgggag tgtc        44

<210> SEQ ID NO 55
<211> LENGTH: 42
<212> TYPE: DNA
<213> ORGANISM: Artificial
<220> FEATURE:
<223> OTHER INFORMATION: primer

<400> SEQUENCE: 55
cgatacgacg ggcgtactag cggctctctt ggcgttcttc ag          42

<210> SEQ ID NO 56
<211> LENGTH: 42
<212> TYPE: DNA
<213> ORGANISM: Artificial
<220> FEATURE:
<223> OTHER INFORMATION: primer

<400> SEQUENCE: 56
cgatacgacg ggcgtactag cgtcattacc agccgacagc ac          42

<210> SEQ ID NO 57
<211> LENGTH: 41
<212> TYPE: DNA
<213> ORGANISM: Artificial
<220> FEATURE:
<223> OTHER INFORMATION: primer

<400> SEQUENCE: 57
cgatacgacg ggcgtactag cgccgtcagc gatctctcca c           41

<210> SEQ ID NO 58

```
<211> LENGTH: 42
<212> TYPE: DNA
<213> ORGANISM: Artificial
<220> FEATURE:
<223> OTHER INFORMATION: primer

<400> SEQUENCE: 58
cgatacgacg ggcgtactag cgcctgtcca ccactccttg tc                           42

<210> SEQ ID NO 59
<211> LENGTH: 42
<212> TYPE: DNA
<213> ORGANISM: Artificial
<220> FEATURE:
<223> OTHER INFORMATION: primer

<400> SEQUENCE: 59
cgatacgacg ggcgtactag cggcttgaaa gggcagttct gg                           42

<210> SEQ ID NO 60
<211> LENGTH: 43
<212> TYPE: DNA
<213> ORGANISM: Artificial
<220> FEATURE:
<223> OTHER INFORMATION: primer

<400> SEQUENCE: 60
cgatacgacg ggcgtactag cgcaggtctc cgattgtgat tgc                          43

<210> SEQ ID NO 61
<211> LENGTH: 43
<212> TYPE: DNA
<213> ORGANISM: Artificial
<220> FEATURE:
<223> OTHER INFORMATION: primer

<400> SEQUENCE: 61
cgatacgacg ggcgtactag cgctctggtg tgtggtgctt ata                          43

<210> SEQ ID NO 62
<211> LENGTH: 40
<212> TYPE: DNA
<213> ORGANISM: Artificial
<220> FEATURE:
<223> OTHER INFORMATION: primer

<400> SEQUENCE: 62
cgatacgacg ggcgtactag cgctcggcac ggcaactgtc                              40

<210> SEQ ID NO 63
<211> LENGTH: 42
<212> TYPE: DNA
<213> ORGANISM: Artificial
<220> FEATURE:
<223> OTHER INFORMATION: primer

<400> SEQUENCE: 63
cgatacgacg ggcgtactag cgatgtggat gacgtttagg ta                           42

<210> SEQ ID NO 64
<211> LENGTH: 41
<212> TYPE: DNA
<213> ORGANISM: Artificial
<220> FEATURE:
<223> OTHER INFORMATION: primer

<400> SEQUENCE: 64
```

```
cgatacgacg ggcgtactag cgggttgatg gcagtcggta a                    41

<210> SEQ ID NO 65
<211> LENGTH: 42
<212> TYPE: DNA
<213> ORGANISM: Artificial
<220> FEATURE:
<223> OTHER INFORMATION: primer

<400> SEQUENCE: 65
cgatacgacg ggcgtactag cgaagaagag ttcatgacgg ac                   42

<210> SEQ ID NO 66
<211> LENGTH: 44
<212> TYPE: DNA
<213> ORGANISM: Artificial
<220> FEATURE:
<223> OTHER INFORMATION: primer

<400> SEQUENCE: 66
cgatacgacg ggcgtactag cgtggttgtt tggttggtta ttcg                 44

<210> SEQ ID NO 67
<211> LENGTH: 42
<212> TYPE: DNA
<213> ORGANISM: Artificial
<220> FEATURE:
<223> OTHER INFORMATION: primer

<400> SEQUENCE: 67
cgatacgacg ggcgtactag cgccgatgac ttatagtatt ga                   42

<210> SEQ ID NO 68
<211> LENGTH: 43
<212> TYPE: DNA
<213> ORGANISM: Artificial
<220> FEATURE:
<223> OTHER INFORMATION: primer

<400> SEQUENCE: 68
cgatacgacg ggcgtactag cgataatctt gatgccactt agc                  43

<210> SEQ ID NO 69
<211> LENGTH: 44
<212> TYPE: DNA
<213> ORGANISM: Artificial
<220> FEATURE:
<223> OTHER INFORMATION: primer

<400> SEQUENCE: 69
cgatacgacg ggcgtactag cggttcttca ggctcaggtc aatc                 44

<210> SEQ ID NO 70
<211> LENGTH: 44
<212> TYPE: DNA
<213> ORGANISM: Artificial
<220> FEATURE:
<223> OTHER INFORMATION: primer

<400> SEQUENCE: 70
cgatacgacg ggcgtactag cgacagcggt atgtactggt cata                 44

<210> SEQ ID NO 71
<211> LENGTH: 42
<212> TYPE: DNA
```

<210> SEQ ID NO 72
<211> LENGTH: 42
<212> TYPE: DNA
<213> ORGANISM: Artificial
<220> FEATURE:
<223> OTHER INFORMATION: primer

<400> SEQUENCE: 71
cgatacgacg ggcgtactag cgtgggaata gtgtgcgtat gc         42

<210> SEQ ID NO 72
<211> LENGTH: 42
<212> TYPE: DNA
<213> ORGANISM: Artificial
<220> FEATURE:
<223> OTHER INFORMATION: primer

<400> SEQUENCE: 72
cgatacgacg ggcgtactag cgacatcacc gcgacgcagc aa         42

<210> SEQ ID NO 73
<211> LENGTH: 40
<212> TYPE: DNA
<213> ORGANISM: Artificial
<220> FEATURE:
<223> OTHER INFORMATION: primer

<400> SEQUENCE: 73
cgatacgacg ggcgtactag cggattccgc gatgccgatg            40

<210> SEQ ID NO 74
<211> LENGTH: 44
<212> TYPE: DNA
<213> ORGANISM: Artificial
<220> FEATURE:
<223> OTHER INFORMATION: primer

<400> SEQUENCE: 74
cgatacgacg ggcgtactag cgcgcccatg tatttagaga accg       44

<210> SEQ ID NO 75
<211> LENGTH: 40
<212> TYPE: DNA
<213> ORGANISM: Artificial
<220> FEATURE:
<223> OTHER INFORMATION: primer

<400> SEQUENCE: 75
cgatacgacg ggcgtactag cgccggcgtc gtgcgcgaaa            40

<210> SEQ ID NO 76
<211> LENGTH: 40
<212> TYPE: DNA
<213> ORGANISM: Artificial
<220> FEATURE:
<223> OTHER INFORMATION: primer

<400> SEQUENCE: 76
cgatacgacg ggcgtactag cgcagccacg tcagccagcc            40

<210> SEQ ID NO 77
<211> LENGTH: 42
<212> TYPE: DNA
<213> ORGANISM: Artificial
<220> FEATURE:
<223> OTHER INFORMATION: primer

<400> SEQUENCE: 77
cgatacgacg ggcgtactag cggagcgaat atctggcaca cc         42

<210> SEQ ID NO 78
<211> LENGTH: 42
<212> TYPE: DNA
<213> ORGANISM: Artificial
<220> FEATURE:
<223> OTHER INFORMATION: primer

<400> SEQUENCE: 78
cgatacgacg ggcgtactag cggggccagg tctagaacga at        42

<210> SEQ ID NO 79
<211> LENGTH: 43
<212> TYPE: DNA
<213> ORGANISM: Artificial
<220> FEATURE:
<223> OTHER INFORMATION: primer

<400> SEQUENCE: 79
cgatacgacg ggcgtactag cgtggagtac aatggtctcg agc       43

<210> SEQ ID NO 80
<211> LENGTH: 44
<212> TYPE: DNA
<213> ORGANISM: Artificial
<220> FEATURE:
<223> OTHER INFORMATION: primer

<400> SEQUENCE: 80
cgatacgacg ggcgtactag cgtttgcatg aagtctgaga acga      44

<210> SEQ ID NO 81
<211> LENGTH: 41
<212> TYPE: DNA
<213> ORGANISM: Artificial
<220> FEATURE:
<223> OTHER INFORMATION: primer

<400> SEQUENCE: 81
cgatacgacg ggcgtactag cgacggcatt acaacggcta g         41

<210> SEQ ID NO 82
<211> LENGTH: 44
<212> TYPE: DNA
<213> ORGANISM: Artificial
<220> FEATURE:
<223> OTHER INFORMATION: primer

<400> SEQUENCE: 82
cgatacgacg ggcgtactag cgcatcttct ggtaatccct gttc      44

<210> SEQ ID NO 83
<211> LENGTH: 42
<212> TYPE: DNA
<213> ORGANISM: Artificial
<220> FEATURE:
<223> OTHER INFORMATION: primer

<400> SEQUENCE: 83
cgatacgacg ggcgtactag cgacagcgtt caatctcgtt gg        42

<210> SEQ ID NO 84
<211> LENGTH: 44
<212> TYPE: DNA
<213> ORGANISM: Artificial
<220> FEATURE:

```
<223> OTHER INFORMATION: primer

<400> SEQUENCE: 84
cgatacgacg ggcgtactag cgagagaatt gcgatacgtt acag          44

<210> SEQ ID NO 85
<211> LENGTH: 44
<212> TYPE: DNA
<213> ORGANISM: Artificial
<220> FEATURE:
<223> OTHER INFORMATION: primer

<400> SEQUENCE: 85
cgatacgacg ggcgtactag cgccttacaa cctattgaca cctg          44

<210> SEQ ID NO 86
<211> LENGTH: 42
<212> TYPE: DNA
<213> ORGANISM: Artificial
<220> FEATURE:
<223> OTHER INFORMATION: primer

<400> SEQUENCE: 86
cgatacgacg ggcgtactag cgacacgaga gctacctgca ga            42

<210> SEQ ID NO 87
<211> LENGTH: 42
<212> TYPE: DNA
<213> ORGANISM: Artificial
<220> FEATURE:
<223> OTHER INFORMATION: primer

<400> SEQUENCE: 87
cgatacgacg ggcgtactag cgtttataca atatgggcag gg            42

<210> SEQ ID NO 88
<211> LENGTH: 44
<212> TYPE: DNA
<213> ORGANISM: Artificial
<220> FEATURE:
<223> OTHER INFORMATION: primer

<400> SEQUENCE: 88
cgatacgacg ggcgtactag cgtcgtaagc tgttcttctg gtac          44

<210> SEQ ID NO 89
<211> LENGTH: 43
<212> TYPE: DNA
<213> ORGANISM: Artificial
<220> FEATURE:
<223> OTHER INFORMATION: primer

<400> SEQUENCE: 89
cgatacgacg ggcgtactag cgtcattgct tgatgaaact gat           43

<210> SEQ ID NO 90
<211> LENGTH: 44
<212> TYPE: DNA
<213> ORGANISM: Artificial
<220> FEATURE:
<223> OTHER INFORMATION: primer

<400> SEQUENCE: 90
cgatacgacg ggcgtactag cgttggatat tcaccgaaca ctag          44
```

<210> SEQ ID NO 91
<211> LENGTH: 43
<212> TYPE: DNA
<213> ORGANISM: Artificial
<220> FEATURE:
<223> OTHER INFORMATION: primer

<400> SEQUENCE: 91
cgatacgacg ggcgtactag cgcttgtgga aatgagtcaa cgg            43

<210> SEQ ID NO 92
<211> LENGTH: 44
<212> TYPE: DNA
<213> ORGANISM: Artificial
<220> FEATURE:
<223> OTHER INFORMATION: primer

<400> SEQUENCE: 92
cgatacgacg ggcgtactag cgaggtagct atatttcgct tgac           44

<210> SEQ ID NO 93
<211> LENGTH: 42
<212> TYPE: DNA
<213> ORGANISM: Artificial
<220> FEATURE:
<223> OTHER INFORMATION: primer

<400> SEQUENCE: 93
cgatacgacg ggcgtactag cggagcgtct acgtcctggt ga             42

<210> SEQ ID NO 94
<211> LENGTH: 42
<212> TYPE: DNA
<213> ORGANISM: Artificial
<220> FEATURE:
<223> OTHER INFORMATION: primer

<400> SEQUENCE: 94
cgatacgacg ggcgtactag cgcattggtt tcgctgtttt ga             42

<210> SEQ ID NO 95
<211> LENGTH: 43
<212> TYPE: DNA
<213> ORGANISM: Artificial
<220> FEATURE:
<223> OTHER INFORMATION: primer

<400> SEQUENCE: 95
cgatacgacg ggcgtactag cgtggaagag tgagggtgga tac            43

<210> SEQ ID NO 96
<211> LENGTH: 43
<212> TYPE: DNA
<213> ORGANISM: Artificial
<220> FEATURE:
<223> OTHER INFORMATION: primer

<400> SEQUENCE: 96
cgatacgacg ggcgtactag cgaataatcc ctctgttgac gaa            43

<210> SEQ ID NO 97
<211> LENGTH: 43
<212> TYPE: DNA
<213> ORGANISM: Artificial
<220> FEATURE:
<223> OTHER INFORMATION: primer

```
<400> SEQUENCE: 97
cgatacgacg ggcgtactag cgaggagcaa tgagaattac acg        43

<210> SEQ ID NO 98
<211> LENGTH: 42
<212> TYPE: DNA
<213> ORGANISM: Artificial
<220> FEATURE:
<223> OTHER INFORMATION: primer

<400> SEQUENCE: 98
cgatacgacg ggcgtactag cgctaagttc caatactctt gc         42

<210> SEQ ID NO 99
<211> LENGTH: 45
<212> TYPE: DNA
<213> ORGANISM: Artificial
<220> FEATURE:
<223> OTHER INFORMATION: primer

<400> SEQUENCE: 99
cgatacgacg ggcgtactag cggccggtac ttatgtatgt gcatt      45

<210> SEQ ID NO 100
<211> LENGTH: 42
<212> TYPE: DNA
<213> ORGANISM: Artificial
<220> FEATURE:
<223> OTHER INFORMATION: primer

<400> SEQUENCE: 100
cgatacgacg ggcgtactag cgcatcattg gcggttgatt ta         42

<210> SEQ ID NO 101
<211> LENGTH: 42
<212> TYPE: DNA
<213> ORGANISM: Artificial
<220> FEATURE:
<223> OTHER INFORMATION: primer

<400> SEQUENCE: 101
cgatacgacg ggcgtactag cggggaacat acgcttccag at         42

<210> SEQ ID NO 102
<211> LENGTH: 43
<212> TYPE: DNA
<213> ORGANISM: Artificial
<220> FEATURE:
<223> OTHER INFORMATION: primer

<400> SEQUENCE: 102
cgatacgacg ggcgtactag cgttccacat tttgtttggg aaa        43

<210> SEQ ID NO 103
<211> LENGTH: 42
<212> TYPE: DNA
<213> ORGANISM: Artificial
<220> FEATURE:
<223> OTHER INFORMATION: primer

<400> SEQUENCE: 103
cgatacgacg ggcgtactag cgccttatcc gactcgcaat gt         42

<210> SEQ ID NO 104
<211> LENGTH: 44
```

```
<212> TYPE: DNA
<213> ORGANISM: Artificial
<220> FEATURE:
<223> OTHER INFORMATION: primer

<400> SEQUENCE: 104
cgatacgacg ggcgtactag cgcagtgtga ggttatgtgg tgga                    44

<210> SEQ ID NO 105
<211> LENGTH: 41
<212> TYPE: DNA
<213> ORGANISM: Artificial
<220> FEATURE:
<223> OTHER INFORMATION: primer

<400> SEQUENCE: 105
cgatacgacg ggcgtactag cgttggttgc gcaattcaag t                       41

<210> SEQ ID NO 106
<211> LENGTH: 43
<212> TYPE: DNA
<213> ORGANISM: Artificial
<220> FEATURE:
<223> OTHER INFORMATION: primer

<400> SEQUENCE: 106
cgatacgacg ggcgtactag cgtgttgttc tttgtgcagg aga                     43

<210> SEQ ID NO 107
<211> LENGTH: 44
<212> TYPE: DNA
<213> ORGANISM: Artificial
<220> FEATURE:
<223> OTHER INFORMATION: primer

<400> SEQUENCE: 107
cgatacgacg ggcgtactag cgtcgtaatg ttagctgtat catc                    44

<210> SEQ ID NO 108
<211> LENGTH: 44
<212> TYPE: DNA
<213> ORGANISM: Artificial
<220> FEATURE:
<223> OTHER INFORMATION: primer

<400> SEQUENCE: 108
cgatacgacg ggcgtactag cgtacattag ctgtccactt accg                    44

<210> SEQ ID NO 109
<211> LENGTH: 43
<212> TYPE: DNA
<213> ORGANISM: Artificial
<220> FEATURE:
<223> OTHER INFORMATION: primer

<400> SEQUENCE: 109
cgatacgacg ggcgtactag cggtgggtgg tggtcttaag ttt                     43

<210> SEQ ID NO 110
<211> LENGTH: 43
<212> TYPE: DNA
<213> ORGANISM: Artificial
<220> FEATURE:
<223> OTHER INFORMATION: primer

<400> SEQUENCE: 110
```
cgatacgacg ggcgtactag cgctggatat taccagtgtc att         43

<210> SEQ ID NO 111
<211> LENGTH: 43
<212> TYPE: DNA
<213> ORGANISM: Artificial
<220> FEATURE:
<223> OTHER INFORMATION: primer

<400> SEQUENCE: 111
cgatacgacg ggcgtactag cgactgataa aggggagtgg ata         43

<210> SEQ ID NO 112
<211> LENGTH: 41
<212> TYPE: DNA
<213> ORGANISM: Artificial
<220> FEATURE:
<223> OTHER INFORMATION: primer

<400> SEQUENCE: 112
cgatacgacg ggcgtactag cgctcgcctt gctctttgag c           41

<210> SEQ ID NO 113
<211> LENGTH: 42
<212> TYPE: DNA
<213> ORGANISM: Artificial
<220> FEATURE:
<223> OTHER INFORMATION: primer

<400> SEQUENCE: 113
cgatacgacg ggcgtactag cgggacacaa gccctctcta cg          42

<210> SEQ ID NO 114
<211> LENGTH: 43
<212> TYPE: DNA
<213> ORGANISM: Artificial
<220> FEATURE:
<223> OTHER INFORMATION: primer

<400> SEQUENCE: 114
cgatacgacg ggcgtactag cgtagatacg gttacggtta cag         43

<210> SEQ ID NO 115
<211> LENGTH: 42
<212> TYPE: DNA
<213> ORGANISM: Artificial
<220> FEATURE:
<223> OTHER INFORMATION: primer

<400> SEQUENCE: 115
cgatacgacg ggcgtactag cgcatgggaa gctgttttga tg          42

<210> SEQ ID NO 116
<211> LENGTH: 42
<212> TYPE: DNA
<213> ORGANISM: Artificial
<220> FEATURE:
<223> OTHER INFORMATION: primer

<400> SEQUENCE: 116
cgatacgacg ggcgtactag cgcccgaaga attgttccaa tc          42

<210> SEQ ID NO 117
<211> LENGTH: 21
<212> TYPE: DNA
<213> ORGANISM: Artificial

```
<220> FEATURE:
<223> OTHER INFORMATION: Primer

<400> SEQUENCE: 117
gaccaatcct gtcacctctg a                                              21

<210> SEQ ID NO 118
<211> LENGTH: 21
<212> TYPE: DNA
<213> ORGANISM: Artificial
<220> FEATURE:
<223> OTHER INFORMATION: Primer

<400> SEQUENCE: 118
gtatatgagk cccatrcaac t                                              21

<210> SEQ ID NO 119
<211> LENGTH: 20
<212> TYPE: DNA
<213> ORGANISM: Artificial
<220> FEATURE:
<223> OTHER INFORMATION: Primer

<400> SEQUENCE: 119
tcggtgggaa agaatttgac                                                20

<210> SEQ ID NO 120
<211> LENGTH: 20
<212> TYPE: DNA
<213> ORGANISM: Artificial
<220> FEATURE:
<223> OTHER INFORMATION: Primer

<400> SEQUENCE: 120
ttcctgatag gggctctgtg                                                20

<210> SEQ ID NO 121
<211> LENGTH: 24
<212> TYPE: DNA
<213> ORGANISM: Artificial
<220> FEATURE:
<223> OTHER INFORMATION: Primer

<400> SEQUENCE: 121
acaagcaagg agatagcata gatg                                           24

<210> SEQ ID NO 122
<211> LENGTH: 24
<212> TYPE: DNA
<213> ORGANISM: Artificial
<220> FEATURE:
<223> OTHER INFORMATION: Primer

<400> SEQUENCE: 122
gtaggagaag gtgtatgagt tagc                                           24

<210> SEQ ID NO 123
<211> LENGTH: 20
<212> TYPE: DNA
<213> ORGANISM: Artificial
<220> FEATURE:
<223> OTHER INFORMATION: Primer

<400> SEQUENCE: 123
acctgggcta attgggattc                                                20
```

<210> SEQ ID NO 124
<211> LENGTH: 20
<212> TYPE: DNA
<213> ORGANISM: Artificial
<220> FEATURE:
<223> OTHER INFORMATION: Primer

<400> SEQUENCE: 124
aatgcctgtt ggagcttgtt                                               20

<210> SEQ ID NO 125
<211> LENGTH: 20
<212> TYPE: DNA
<213> ORGANISM: Artificial
<220> FEATURE:
<223> OTHER INFORMATION: Primer

<400> SEQUENCE: 125
ggcttatgtg gccccttact                                               20

<210> SEQ ID NO 126
<211> LENGTH: 20
<212> TYPE: DNA
<213> ORGANISM: Artificial
<220> FEATURE:
<223> OTHER INFORMATION: Primer

<400> SEQUENCE: 126
aagatggccg cgtattattg                                               20

<210> SEQ ID NO 127
<211> LENGTH: 20
<212> TYPE: DNA
<213> ORGANISM: Artificial
<220> FEATURE:
<223> OTHER INFORMATION: Primer

<400> SEQUENCE: 127
ggctcagata tgcgagaaca                                               20

<210> SEQ ID NO 128
<211> LENGTH: 21
<212> TYPE: DNA
<213> ORGANISM: Artificial
<220> FEATURE:
<223> OTHER INFORMATION: Primer

<400> SEQUENCE: 128
ttggtccggg taataatgag a                                             21

<210> SEQ ID NO 129
<211> LENGTH: 20
<212> TYPE: DNA
<213> ORGANISM: Artificial
<220> FEATURE:
<223> OTHER INFORMATION: Primer

<400> SEQUENCE: 129
ccatatgcgg cattataccc                                               20

<210> SEQ ID NO 130
<211> LENGTH: 20
<212> TYPE: DNA
<213> ORGANISM: Artificial
<220> FEATURE:
<223> OTHER INFORMATION: Primer

<400> SEQUENCE: 130
gcagtctctc tgcgttttcc                                        20

<210> SEQ ID NO 131
<211> LENGTH: 20
<212> TYPE: DNA
<213> ORGANISM: Artificial
<220> FEATURE:
<223> OTHER INFORMATION: Primer

<400> SEQUENCE: 131
tgctttaccc aaggcaaaaa                                        20

<210> SEQ ID NO 132
<211> LENGTH: 20
<212> TYPE: DNA
<213> ORGANISM: Artificial
<220> FEATURE:
<223> OTHER INFORMATION: Primer

<400> SEQUENCE: 132
agcctcatct gccaggtcta                                        20

<210> SEQ ID NO 133
<211> LENGTH: 23
<212> TYPE: DNA
<213> ORGANISM: Artificial
<220> FEATURE:
<223> OTHER INFORMATION: Primer

<400> SEQUENCE: 133
aagatggctc ttagcaaagt caa                                    23

<210> SEQ ID NO 134
<211> LENGTH: 22
<212> TYPE: DNA
<213> ORGANISM: Artificial
<220> FEATURE:
<223> OTHER INFORMATION: Primer

<400> SEQUENCE: 134
tactatctcc tgtgctccgt tg                                     22

<210> SEQ ID NO 135
<211> LENGTH: 20
<212> TYPE: DNA
<213> ORGANISM: Artificial
<220> FEATURE:
<223> OTHER INFORMATION: Primer

<400> SEQUENCE: 135
tggggcaaat acaaagatgg                                        20

<210> SEQ ID NO 136
<211> LENGTH: 23
<212> TYPE: DNA
<213> ORGANISM: Artificial
<220> FEATURE:
<223> OTHER INFORMATION: Primer

<400> SEQUENCE: 136
cacatcataa ttgggagtgt caa                                    23

<210> SEQ ID NO 137

```
<211> LENGTH: 21
<212> TYPE: DNA
<213> ORGANISM: Artificial
<220> FEATURE:
<223> OTHER INFORMATION: Primer

<400> SEQUENCE: 137
ccaaccaaac aacaacgttc a                                              21

<210> SEQ ID NO 138
<211> LENGTH: 20
<212> TYPE: DNA
<213> ORGANISM: Artificial
<220> FEATURE:
<223> OTHER INFORMATION: Primer

<400> SEQUENCE: 138
accttgactg gaggccgtta                                                20

<210> SEQ ID NO 139
<211> LENGTH: 32
<212> TYPE: DNA
<213> ORGANISM: Artificial
<220> FEATURE:
<223> OTHER INFORMATION: Primer

<400> SEQUENCE: 139
tcaactcgaa taacggtgac ttcttaccac tg                                  32

<210> SEQ ID NO 140
<211> LENGTH: 22
<212> TYPE: DNA
<213> ORGANISM: Artificial
<220> FEATURE:
<223> OTHER INFORMATION: Primer

<400> SEQUENCE: 140
tgcagagcgt cctttggtct at                                             22

<210> SEQ ID NO 141
<211> LENGTH: 25
<212> TYPE: DNA
<213> ORGANISM: Artificial
<220> FEATURE:
<223> OTHER INFORMATION: Primer

<400> SEQUENCE: 141
ctcttactcg tggtttccaa cttga                                          25

<210> SEQ ID NO 142
<211> LENGTH: 24
<212> TYPE: DNA
<213> ORGANISM: Artificial
<220> FEATURE:
<223> OTHER INFORMATION: Primer

<400> SEQUENCE: 142
tggcgcccat aagcaacact cgaa                                           24

<210> SEQ ID NO 143
<211> LENGTH: 25
<212> TYPE: DNA
<213> ORGANISM: Artificial
<220> FEATURE:
<223> OTHER INFORMATION: Primer

<400> SEQUENCE: 143
```

```
aacagatgta agcagctccg ttatc                                                25

<210> SEQ ID NO 144
<211> LENGTH: 26
<212> TYPE: DNA
<213> ORGANISM: Artificial
<220> FEATURE:
<223> OTHER INFORMATION: Primer

<400> SEQUENCE: 144
cgatttttat tggatgctgt acattt                                               26

<210> SEQ ID NO 145
<211> LENGTH: 26
<212> TYPE: DNA
<213> ORGANISM: Artificial
<220> FEATURE:
<223> OTHER INFORMATION: Primer

<400> SEQUENCE: 145
tgccatagca tgacacaatg gctcct                                               26

<210> SEQ ID NO 146
<211> LENGTH: 21
<212> TYPE: DNA
<213> ORGANISM: Artificial
<220> FEATURE:
<223> OTHER INFORMATION: Primer

<400> SEQUENCE: 146
cggcagcgtc tcaattcgtt c                                                    21

<210> SEQ ID NO 147
<211> LENGTH: 20
<212> TYPE: DNA
<213> ORGANISM: Artificial
<220> FEATURE:
<223> OTHER INFORMATION: Primer

<400> SEQUENCE: 147
caagccgcct tcctcatagc                                                      20
```

MULTIPLEXED POLYMERASE CHAIN REACTION FOR GENETIC SEQUENCE ANALYSIS

This application claims priority to U.S. Provisional Patent Application Nos. 60/691,768, filed on Jun. 16, 2005; 60/735,876 filed on Nov. 14, 2005; 60/735,824 filed on Nov. 14, 2005; and 60/743,639, filed on Mar. 22, 2006, all incorporated herein by reference. This application is a continuation-in-part application of U.S. patent application Ser. Nos. 11/177,647, filed Jul. 2, 2005; 11/177,646, filed Jul. 2, 2005; and 11/268,373, filed on Nov. 7, 2005, all incorporated herein by reference. These nonprovisional applications claim priority to U.S. Provisional Patent Application Nos. 60/590,931, filed on Jul. 2, 2004; 60/609,918, filed on Sep. 15, 2004; 60/626,500, filed on Nov. 5, 2004; 60/631,437, filed on Nov. 29, 2004; and 60/631,460, filed on Nov. 29, 2004, all incorporated herein by reference. U.S. patent application Ser. No. 11/422,431 is incorporated herein by reference. The attached Sequence Listing submitted on paper is incorporated by reference.

FIELD OF THE INVENTION

The invention relates generally to amplification methods of multiple genetic targets and analysis of amplified products using microarrays.

DESCRIPTION OF RELATED ART

Accurate and rapid identification of infectious pathogens causing acute respiratory infections (ARI) in humans can be a critical factor in the successful treatment of respiratory illness, the application of appropriate outbreak control measures, and the efficient use of precious antibiotics and antiviral drugs. However, clinical differential diagnosis of ARI is challenging due to the similarity of the symptoms caused by different pathogens and the number and biological diversity of those agents. Currently, the most widely used methods for respiratory pathogen identification are culture, immunoassay, and RT-PCR/PCR assays. Culture and immunoassay techniques are generally specific to a particular pathogen, and as such are limited to detecting a single suspected agent at the species and sometimes serotype levels. In contrast, nucleic acid based techniques such as RT-PCR/PCR are versatile, offering high sensitivity in the detection of all pathogens, including fastidious or otherwise difficult-to-culture organisms. Because of the versatile nature of PCR, the technique can be applied simultaneously to multiple agents, increasing the chances of establishing specific etiology (McDonough et al., "A multiplex PCR for detection of *Mycoplasma pneumoniae, Chlamydophila pneumoniae, Legionella pneumophila,* and *Bordetella pertussis* in clinical specimens" *Mol. Cell Probes,* 19, 314-322 (2005)) and allowing accurate detection of simultaneous infections involving more than one pathogen (Grondahl et al., "Rapid identification of nine microorganisms causing acute respiratory tract infections by single-tube multiplex reverse transcription-PCR: feasibility study" *J. Clin. Microbiol.,* 37, 1-7 (1999)). (All referenced publications and patent documents are incorporated herein by reference.)

Detection of several organisms within one reaction by multiplex approaches is desirable since ARI agents can be symptomologically nonspecific. Thus, assaying for one pathogen at a time is inefficient and does not produce information regarding possible co-infections. Several multiplex RT-PCR/PCR tests have been developed to address this (McDonough; Grondahl; Puppe et al., "Evaluation of a multiplex reverse transcriptase PCR ELISA for the detection of nine respiratory tract pathogens" *J. Clin. Virol.,* 30, 165-174 (2004); Bellau-Pujol et al., "Development of three multiplex RT-PCR assays for the detection of 12 respiratory RNA viruses" *J. Virol. Methods,* 126, 53-63 (2005); Miyashita et al., "Multiplex PCR for the simultaneous detection of *Chlamydia pneumoniae, Mycoplasma pneumoniae* and *Legionella pneumophila* in community-acquired pneumonia" *Respir. Med.,* 98, 542-550 (2004); Osiowy, "Direct detection of respiratory syncytial virus, parainfluenza virus, and adenovirus in clinical respiratory specimens by a multiplex reverse transcription-PCR assay" *J. Clin. Microbiol.,* 36, 3149-3154 (1998); Verstrepen et al., "Rapid detection of enterovirus RNA in cerebrospinal fluid specimens with a novel single-tube real-time reverse transcription-PCR assay" *J. Clin. Microbiol.,* 39, 4093-4096 (2001); Coiras et al., "Simultaneous detection of fourteen respiratory viruses in clinical specimens by two multiplex reverse transcription nested-PCR assays" *J. Med. Virol.,* 72, 484-495 (2004); Coiras et al., "Oligonucleotide array for simultaneous detection of respiratory viruses using a reverse-line blot hybridization assay" *J. Med. Virol.,* 76, 256-264 (2005); Gruteke et al., "Practical implementation of a multiplex PCR for acute respiratory tract infections in children" *J. Clin. Microbiol.,* 42, 5596-5603 (2004)) but the approach is limited by the discriminating power of current amplicon detection methods. Gel-based analysis approaches tend to be restricted to a limited number of pathogens whose products can be discriminated by size alone while fluorescent reporter systems like real-time PCR are limited by the number of the fluorescent peaks that can be unequivocally resolved—no more than three or four. Thus, there is a need for diagnostic assays that allow rapid differentiation and identification of the pathogens responsible for disease syndromes with many potential causes, such as ARI.

A few technologies have been developed that allow more pathogens to be detected simultaneously by RT-PCR/PCR methods. Multiplex identification of up to 22 respiratory pathogens has been achieved by the MASSCODE™ multiplex RT-PCR system (Briese et al., "Diagnostic system for rapid and sensitive differential detection of pathogens" *Emerg. Infect. Dis.,* 11, 310-313 (2005)). Spotted (especially long-oligonucleotide) microarrays have also been used with some success as a multiplex PCR analysis tool (Roth et al., "Use of an oligonucleotide array for laboratory diagnosis of bacteria responsible for acute upper respiratory infections" *J. Clin. Microbiol.,* 42, 4268-4274 (2004); Chizhikov et al., "Microarray analysis of microbial virulence factors" *Appl. Environ. Microbiol.,* 67, 3258-3263 (2001); Chizhikov et al., "Detection and genotyping of human group A rotaviruses by oligonucleotide microarray hybridization" *J. Clin. Microbiol.,* 40, 2398-2407 (2002); Wang et al., "Microarray-based detection and genotyping of viral pathogens" *Proc. Natl. Acad. Sci. USA,* 99, 15687-15692 (2002); Wang et al., "Viral discovery and sequence recovery using DNA microarrays" *PLoS Biol.,* 1, E2 (2003); Wilson et al., "High-density microarray of small-subunit ribosomal DNA probes" *Appl. Environ. Microbiol.,* 68, 2535-2541 (2002); Wilson et al., "Sequence-specific identification of 18 pathogenic microorganisms using microarray technology" *Mol. Cell. Probes,* 16, 119-127 (2002); Call et al., "Identifying antimicrobial resistance genes with DNA microarrays" *Antimicrob. Agents Chemother.,* 47, 3290-3295 (2003); Call et al., "Mixed-genome microarrays reveal multiple serotype and lineage-specific differences among strains of *Listeria monocytogenes" J. Clin. Microbiol.,* 41, 632-639 (2003). The primary limitation of these systems is the inability to discriminate closely related strains of the same organism because the detected hybridization events may be insensitive to partial sequence divergence. For instance, spotted microarray probes may cross-hybridize nonspecifically with sequences that vary by as much as 25%—an unfortunate event considering the fact that this invisible variation carries enough information to allow a high degree of strain differentiation if the polymorphisms could be specifically defined.

Strain-level identification can be critical in cases where closely related organisms can have very different clinical consequences and epidemiological patterns. In such cases, strains must be discriminated to allow proper treatment and control. The clinically relevant *Bordetella pertussis* and its sister species, the clinically irrelevant *B. parapertussis*, offer a classic example. Another example is influenza viruses, for which discrimination of vaccine-sensitive and -insensitive strains, as well as circulating human isolates and possible zoonotic strains (e.g. avian H5N1) is of immediate and obvious value.

SUMMARY OF THE INVENTION

The invention comprises a method comprising: providing a biological sample suspected of containing one or more pathogen nucleic acids from a predefined set of pathogens; adding to the sample a plurality of PCR primers corresponding to genes found in the predefined set of pathogens; and performing a polymerase chain reaction on the sample to amplify a subset of the nucleic acids that correspond to the genes. The primers include at least one primer pair for each pathogen, and the primers comprise a tail sequence that is not homologous any pathogen DNA or to any background DNA in the sample. The concentration of at least one primer in the polymerase chain reaction is no more than about 100 nM.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Clinical syndromes are seldom specific to single pathogens, so assays that allow testing for, and discriminating among, a large number of candidate pathogens will undoubtedly be beneficial to public health efforts. The work presented here demonstrates the clinical diagnostic and epidemiological surveillance potentials of a resequencing array (RA) approach that combines multiplex RT-PCR/PCR, RA, and automated sequence similarity searching and pathogen identification—the RPM v.1 system, for 20 common respiratory pathogens, as well as 6 biothreat agents under a broad spectrum of conditions. By combining the sensitivity of multiplex PCR amplification with the specificity of a RA, the trade-off between specificity and sensitivity that is often seen when evaluating diagnostic assays may be averted. This was demonstrated using control samples whether in extraction buffer or together as complex mixtures spiked into healthy patient clinical samples. The data also shows that the system offers equivalent sensitivity to accepted RT-PCR/PCR- and culture-based methods for both HAdV and influenza A virus, using 101 throat-swab samples from patients with influenza-like illness.

Short-oligonucleotide resequencing arrays (RA) may simultaneously provide both species-level and strain-level identification of PCR amplicons from ARI pathogens. Strain-specific information, including unique polymorphisms from previously unrecognized variants, is provided by the RA's ability to reveal sequence differences that distinguish the hybridized target from the prototype sequences (ProSeqs, see U.S. patent application Ser. No. 11/422,431) tiled on the array. Prior studies combined a custom designed Respiratory Pathogen Microarray (RPM v.1) with methods for microbial nucleic acid enrichment, random nucleic acid amplification and automated sequence similarity searching to achieve broad-spectrum respiratory tract pathogen identification at both species and strain levels with unambiguous statistical interpretation (Lin et al., "Broad-spectrum respiratory tract pathogen identification using resequencing DNA microarrays" *Genome Res.*, 16(4), 527-535 (2006); Wang et al., "Rapid, Broad-spectrum Identification of Influenza Viruses by Resequencing Microarrays" *Emerg. Infect. Dis.*, 12(4), 638-646 (2006)). However, generic amplification methods had limited success when dealing with clinical samples that have lower titer of pathogens. Disclosed herein is an improved multiplex PCR amplification strategy that mitigates the sensitivity issue related to random target amplification. Successful proof-of-concept experiments, utilizing clinical samples obtained from patients presenting ARI, demonstrate that high species-level concordance with standard reference assays (e.g. culture, College of American Pathologist [CAP]-certified PCR) can be achieved while still producing correct species and strain-level identification via direct sequence reads in an improved assay time (8.5 hours). The results suggest that this approach is amenable to a straightforward automation and miniaturization process and thus could lead to a microarray-based platform for both diagnostics and surveillance purposes.

Contrary to popular trends: (1) the PCR primer concentrations have been decreased instead of increased to achieve the desired sensitivity, and (2) simultaneous and effective amplifications of targets ranging from 100-2800 base pairs have been performed, which has not been previously demonstrated. These variations were made possible by the use of direct sequence analysis of the amplicons using a resequencing microarray (RA). The RPM v.1, coupled with the pathogen identification algorithms in the cross-referenced application, is not prone to false positives or false negatives caused by signal intensity variations or spurious amplicon cross-reactions. However, all types of lower density microarrays that are incapable of resolving individual base calls with high accuracy will suffer from these artifacts, and hence are not amenable to coupling with the multiplex PCR parameters described herein.

The polymerase chain reaction (PCR) is well known in the art. The present method uses a biological sample that may contain pathogen nucleic acids. The method does not require the presence of the pathogen nucleic acids, as the method may be performed on, for a example, a specimen from a healthy individual. As a preliminary step, the pathogen nucleic acids may be extracted from a clinical sample such as, but not limited to, a nasal wash, a throat swab, sputum, blood, or an environmental sample. The clinical sample may be obtained from an organism of any species including, but are not limited to, humans. Any type of pathogen may be tested for including, but not limited to, respiratory pathogens, enteric pathogens, and biothreat agents such as anthrax spores. The set of pathogens may be defined at, for example, the species level or the strain level.

The method involves PCR primers that correspond to genes that may be found in the pathogens. PCR primers are well known in the art. There is at least one primer pair for each pathogen. The primers used in the method have a tail sequence that is not homologous to the DNA of any of the pathogens or to any background DNA in the sample. The background DNA may be the DNA of the species from which a clinical sample was obtained. Potential tail sequences may be randomly or otherwise generated and may be evaluated by, for example, comparison to a database of genetic sequences, such as GenBank. The tail sequence generally does not itself bind to the pathogen DNA and may reduce the formation of primer-dimers in the PCR, as the tail is not complementary to any other primer. Suitable tails for use with a specimen obtained from humans include, but are not limited to, CGATACGACGGGCGTACTAGCG (Primer L, SEQ ID NO. 1) and CGATACGACGGGCGTACTAGCGNNNNNNNNN (Primer LN, SEQ ID NO. 2).

The set of primers in single PCR may include, for example, at least 30, 40, 50, 60, 70, 80, 90, or 100 different primers. Primers corresponding to genes of varying lengths may be used in the same PCR. For example, amplified nucleic acids of lengths less than 50, 100, or 200 and more than 3000 or 2000 nucleotides may be produced in a single PCR.

A PCR using these primers may include other components or use equipment as generally known in the field of PCR and as disclosed herein. Low concentrations of primers may be used in the reaction. From one to all of the primers may be present at a concentration of no more than about 100 nM. Lower concentrations such as 40-50 nM may be used.

The biological sample may be divided into a plurality of aliquots and a separate PCR using different primers performed on each aliquot. The aliquots may then be recombined after the PCR. This may be done when a large number of primers is used. The more primers that are used in a PCR, the more likely is the formation of primer-dimers. The PCR may be better optimized with multiple aliquots with different primer mixes.

After the PCR, an identification of the pathogen may be performed. This may be done by contacting the sample to a microarray comprising a plurality of nucleic acid sequences that are complementary to at least portions of the amplified nucleic acids, and allowing the amplified nucleic acids to hybridize to complementary nucleic acids. Such methods are described in U.S. patent application Ser. No. 11/177,646. The complementary nucleic acids may be, but are not limited to, from 25- to 29-mers. The use of such short complementary nucleic acids reduces the possibility that any mismatches will hybridize to the microarray. The complementary nucleic acids may include a perfect match probe to at least one of and up to all of the amplified nucleic acids and three different single nucleotide polymorphisms of the center position of each perfect match probe. This arrangement allows for the entire sequence of the gene to be determined, which can allow for identification of the strain of the pathogen.

After hybridization, known methods, such as fluorescence, may be used to detect which complementary nucleic acids have hybridized amplified nucleic acids. When specific PCR is used to amplify the targets, a very high signal-to-noise (S/N) optical signal is obtained from each respective hybridization site on the array. In combination with a resequencing array, the sensitivity and specificity can be greater than with a specific PCR assay alone. Thus, a resequencing array provides a digital, not an analog readout. It is dependent only on a S/N ratio, not on an absolute optical intensity (above a baseline minimum). This means that amplicons that are in too few in quantity to be detected can still satisfy the resequencing "logic function", even at barely detectable absolute signal intensities, provided that background "noise" on the array is low enough. Base calls may be estimated by comparing the respective intensities for the sense and antisense probe sets. The pathogen may then be identified based on which amplified nucleic acids are detected. This may be done by a pattern recognition algorithm, where the pathogen is identified based on which genes are hybridized to the array. It may also be done based on sequencing of the hybridized genes, as described above.

Molecular diagnostic techniques enable rapid and sensitive identification of etiological agents. Current methods, such as PCR, RT-PCR, and spotted microarray etc., are vulnerable to misidentification due to false positive and false negative test results, and tend to suffer from a direct tradeoff between sensitivity and specificity. Samples consist of a large and diverse group of background organisms which may also contain regions of similarity to the target sequence used for diagnostic PCR amplification. The genetic complexity of non-target DNA (especially human DNA) may cause the amplification of a "false positive" product due to cross reactivity. In addition, viruses evolve through mutation and recombination events at a very fast rate, making particularly sensitive tests subject to a state of constant redesign or almost immediate obsolescence. Genetic variations are also clinically relevant, as they may correlate to antigenic variations which have potential implications for persistence of infection and the response to treatment and/or vaccination. To study genetic variation with current PCR methods, additional sequencing steps are always required. The RPM v.1 method not only detects infectious agents at the species and strain levels, but can also identify subtle genomic differences without further experiment. This approach is also shown to be an effective means for detecting up to 7 pathogens simultaneously with high sensitivity and specificity, and allow unambiguous and reproducible sequence-based strain identification for pathogens with appropriately selected prototype sequence on the microarray (ProSeqs). This may be useful for enhancing clinical management and epidemic outbreak responses by permitting accurate fingerprinting, antibiotic resistance profiling, genetic drift/shift analysis, forensics, and many other parameters of each pathogen. This capability may be invaluable for rapid detection of emerging diseases, such as avian H5N1 influenza virus, and biological terrorism events.

Having described the invention, the following examples are given to illustrate specific applications of the invention. These specific examples are not intended to limit the scope of the invention described in this application.

Example 1

RPM v.1 chip design—The RPM v.1 (Respiratory Pathogen Microarray) chip design, included 57 tiled regions allowing resequencing of 29.7 kb of sequences from 27 respiratory pathogens and biowarfare agents, and was described in detail in a previous study (Lin et al., "Broad-spectrum respiratory tract pathogen identification using resequencing DNA microarrays" *Genome Res.*, 16(4), 527-535 (2006)). Briefly, RPM arrays consist of sequential 25-mer perfect match probes representing (and centered on) each base in a sequence chosen from the genome of the target organisms. Furthermore, for each perfect match probe, three mismatch probes representing the three possible single nucleotide polymorphisms (SNPs) of the center position were also tiled on the array. Thus hybridization to a series of perfect matches provides redundant presence/absence information, while hybridization to mismatched probes reveals strain-specific SNP data. On this chip, two pathogens, HAdV and influenza A were given more probe representation than others. These were selected based upon clinical relevance for the population of immediate interest (United States military recruit in training). For HAdV, partial sequences from the E1A, hexon, and fiber genes containing diagnostic regions of serotypes 4, 5, and 7 were tiled for the detection of all ARI-associated HAdVs. Similarly, tiled regions for influenza A virus detection were comprised of partial sequences from the hemagglutinin (subtypes H1, H3, and H5), the neuraminidase (subtypes N1 and N2), and the matrix genes. In addition to 3 HAdVs and 3 influenza A viruses, the current RPM design permits discrimination of 15 other common respiratory pathogens, and 6 Centers for Disease Control and Prevention category A bioterrorism pathogens (Table 1) known to cause ARI, i.e. "flu-like" symptoms at early stages of infection. All control and field strains used to test the sensitivity and specificity of RPM v.1 and their sources are listed in Table 1.

Example 2

Clinical samples—Archived throat swabs were collected from patients with ARI symptoms at various military recruit training centers, US/Mexico border sites, and on deployed naval ships from 1999-2005. These were immediately placed in 2 mL cryogenic vials containing 1.5 mL of viral transport medium (VTM), frozen and stored at or below −80° C. to maintain the viral particles during transport. Samples were then shipped to the Naval Health Research Center (NHRC, San Diego, Calif.), thawed and aliquoted, and tested for HAdV and influenza using CAP-certified diagnostic RT-PCR/PCR and culture tests. Frozen aliquots were then submitted for microarray-based detection in a blinded fashion.

Example 3

Nucleic acid extraction—Nucleic acid was extracted from clinical samples using either the MASTERPURE™ DNA

TABLE 1

Analytic sensitivity of microarray-based detection for prototype control strains.

| Organism | Sample Type | Strain | Sample Source | Detection limit (genome copies) |
|---|---|---|---|---|
| HAdV-4[@] | DNA | RI-67 | ATCC | 100 |
| HAdV-4 vaccine | DNA | CL68578 | NHRC | 100 |
| HAdV-4FS_Navy | DNA | | NRHC | 100 |
| HAdV-4FS_AirForce | DNA | | AFIOH | 100 |
| HAdV-4FS_AirForce | Viral particles | | ADL | 100 |
| HAdV-5 | DNA | adenoid 75 | ATCC | 1000 |
| HAdV-7 | DNA | Gomen | ATCC | 100 |
| HAdV-7 | Viral particles | Gomen | ATCC | N.D. |
| HAdV-7a vaccine | DNA | 55142 | NHRC | 100 |
| HAdV-7FS_Navy | DNA | | NHRC | 1000 |
| B. anthracis | DNA | AMES | AFIP | 10* |
| B. anthracis | Bacterial cells | STERNE | CRP | N.D. |
| B. pertussis | DNA | | NHRC | 100 |
| C. pneumoniae | DNA | | ABi | 10* |
| Influenza A-H1N1 | Viral particles | PR/8/34 | ABi | 100 |
| Influenza A-H3N2 | RNA | | ADL | 100 |
| Influenza A-H5N1 | RNA | | AFIOH | 10* |
| Influenza B | Viral particles | B/Lee/40 | ABi | 1000 |
| F. tularensis | DNA | SCHU4 | ATCC | 1000 |
| F. tularensis | Bacterial cells | SCHU4 | CRP | N.D. |
| Human coronavirus | NA | 229E | ATCC | 1000 |
| Human coronavirus | Viral particles | 229E | ATCC | N.D. |
| Human coronavirus | NA | OC43 | ATCC | 1000 |
| Human coronavirus | Viral particles | OC43 | ATCC | N.D. |
| Rhinovirus 89 | Viral particles | 41467 Gallo | ATCC | 1000 |
| Lassa Virus[#] | plasmids | | BlueHeron | 1000 |
| M. pneumoniae | DNA | | AFIP | 1000 |
| M. pneumoniae | Bacterial cells | | NHRC | N.D. |
| N. meningitidis | DNA | Murray | ATCC | 100 |
| Parainfluenza Virus 1 | Viral particles | C-35 | ATCC | 1000 |
| Parainfluenza Virus 3 | Viral particles | C 243 | ATCC | 1000 |
| RSV A | Viral particles | A-2 | ATCC | 1000 |
| RSV B | Viral particles | B WV/14617/85 | ATCC | 100 |
| S. pneumoniae | DNA | | AFIP | 100 |
| S. pyogenes | DNA | Rosenbach | ATCC | 1000 |
| S. pyogenes | Bacterial cells | | NHRC | N.D. |
| Variola Major Virus[#] | plasmids | | BlueHeron | 1000 |
| Vaccinia | DNA | Lister | ABi | 1000 |
| Y. pestis | DNA | D27 | AFIP | 1000 |
| Y. pestis | Bacterial cells | CO92 | CRP | N.D. |
| Ebola Virus[#] | plasmids | | BlueHeron | 1000 |

Note:
[@]plaque purified;
*the lowest detection limit tested;
[#]target genes were constructed and cloned into pUC119 by BlueHeron Biotechnology (Bothell, WA).

purification kit (Epicentre Technologies, Madison, Wis.), omitting RNase digestion, or the MagNA Pure Compact Nucleic Acid Isolation Kit I (Roche Applied Science, Indianapolis, Ind.) following the manufacturer's recommended protocols.

Example 4

Internal controls—Two *Arabidopsis thaliana* genes, corresponding to NAC1 and triosphosphate isomerase (TIM), were chosen as internal controls for reverse transcription (RT) and PCR reactions as they would be unlikely to occur naturally in clinical samples. Two plasmids, pSP64poly(A)-NAC1 and pSP64poly(A)-TIM, containing ~500 bp of the two genes were kindly provided by Dr. Norman H. Lee at The Institute for Genome Research (Rockville, Md.). NAC1 was amplified by PCR with SP6 and M13R primers, and the PCR products were purified using QIAquick PCR Purification Kit (Qiagen, Valencia, Calif.). To generate RNA from pSP64poly(A)-TIM, the plasmids were linearized with EcoRI and in vitro transcribed from the SP6 promoter using the MEGAS-CRIPT® High Yield Transcription Kit (Ambion, Austin, Tex.). 60 fg each of NAC1 and TIM were used as internal controls for checking the amplification efficiency and the presence of inhibitors in the specimens.

Example 5

Primer design and Multiplex RT-PCR amplification—Dividing the primers into two independent reactions simplified primer design and optimization. Fine-tuning adjustments to both mixtures (swapping primers that amplified poorly for new ones) were carried out to ensure all target genes from the 26 targeted pathogens (West Nile Virus is included on the array but not in this amplification scheme) would amplify sufficiently to allow hybridization. The gene-specific primer pairs for all targets on the RPM v.1 chip (listed Tables 2(a) and 2(b)) were designed to ensure good amplification efficiency for multiplex PCR. All primers were designed to have a similar annealing temperature, and checked to ensure uniqueness using a full search of the GenBank database with the BLAST program for known sequences. All primers were checked for potential hybridization to other primers to reduce the potential of primer-dimer formation. In addition, we adapted a method developed by Shuber et al., "A simplified procedure for developing multiplex PCRs" *Genome Res.*, 5, 488-493 (1995) and Brownie et al., "The elimination of primer-dimer accumulation in PCR" *Nucleic Acids Res.*, 25, 3235-3241 (1997) to further suppress primer-dimer formation by adding a linker sequence of 22 bp (primer L) to the 5'-end of primers used in this study. Reverse transcription (RT) reactions were performed in 20 μl volumes containing 50 mM Tris-HCl (pH 8.3), 75 mM KCl, 3 mM $MgCl_2$, 500 μM each of dATP, dCTP, dGTP, dTTP, 40 U of RNaseOUT™, 10 mM DTT, 2 μM primer LN, 200 U of Superscript III (Invitrogen Life Technologies, Carlsbad, Calif.), 60 fg each of two internal controls (NAC1 and TIM), and 5-8 μl of extracted clinical specimen or laboratory control. Reactions were carried out in a Peltier Thermal Cycler-PTC240 DNA Engine Tetrad 2 (MJ Research Inc., Reno, Nev.) using the manufacturer's recommended protocol.

TABLE 2(a)

List of PCR primers in primer mix A used for multiplex PCR

| Primer name | Sequence (5'-3') | SEQ ID NO. | Organism gene | Amplicon size |
|---|---|---|---|---|
| FluAHA1-F2 | CGA TAC GAC GGG CGT ACT AGC GGC CAA CAA CTC AAC CGA CAC | 3 | Influenza A | 810 bp |
| FluAHA1-R2 | CGA TAC GAC GGG CGT ACT AGC GAC ACT TCG CAT CAC ATT CAT CC | 4 | hemaggultinin | |
| FluAHA3-F6 | CGA TAC GAC GGG CGT ACT AGC GAC TTC CCG GAA ATG ACA ACA | 5 | Influenza A | 873 bp |
| FluAHA3-R7 | CGA TAC GAC GGG CGT ACT AGC GGG TTT GTC ATT GGG AAT GCT | 6 | hemaggultinin | |
| FluAHA5-F2 | CGA TAC GAC GGG CGT ACT AGC GGC CAT TCC ACA ACA TAC ACC | 7 | Influenza A | 736 bp |
| FluAHA5-R2 | CGA TAC GAC GGG CGT ACT AGC GAG CTA CCA TGA TTG CCA GTG | 8 | hemaggultinin | |
| FluANA1-F5 | CGA TAC GAC GGG CGT ACT AGC GAC GTT GTT GCT GGA AAG GAC | 9 | Influenza A | 1000 bp |
| FluANA1-R6 | CGA TAC GAC GGG CGT ACT AGC GAA ACT TCC GCT GTA CCC TGA | 10 | neuraminidase | |
| FluANA2-F6 | CGA TAC GAC GGG CGT ACT AGC GGG AAA TAT GCC CCA AAC TAG C | 11 | Influenza A | 1029 bp |
| FluANA2-R6 | CGA TAC GAC GGG CGT ACT AGC GAT GCA GCT TTT GCC TTC AAC | 12 | neuraminidase | |
| FluAMA-F4 | CGA TAC GAC GGG CGT ACT AGC GTT CTA ACC GAG GTC GAA ACG | 13 | Influenza A | 891 bp |
| FluAMA-R5 | CGA TAC GAC GGG CGT ACT AGC GCT CTG GCA CTC CTT CCG TAG | 14 | matrix | |
| FluBHA-F5 | CGA TAC GAC GGG CCT ACT AGC GGG GAG GTC AAT GTG ACT GGT | 15 | Influenza B | 898 bp |
| FluBHA-R5 | CGA TAC GAC GGG CGT ACT AGC GGG GCA ATT TCC TAT GGC TTT | 16 | hemaggultinin | |
| FluBNA-F4 | CGA TAC GAC GGG CGT ACT AGC GGT GAA CCG TTC TGC AAC AAA | 17 | Influenza B | 899 bp |
| FluBNA-R3 | CGA TAC GAC GGG CGT ACT AGC GCC AAT CTT GGA TGC CAT TCT | 18 | neuraminidase | |
| FluBMA-F2 | CGA TAC GAC GGG CGT ACT AGC GCA TTG ACA GAA GAT GGA GAA GG | 19 | Influenza B | 411 bp |
| FluBMA-R2 | CGA TAC GAC GGG CGT ACT AGC GAA GCA CAG AGC GTT CCT AG | 20 | matrix | |
| Ad5 hexon-F2 | CGA TAC GAC GGG CGT ACT AGC GCT GTG GAC CGT GAG GAT ACT | 21 | Adenovirus 5 | 1768 bp |
| Ad5 hexon-R2 | CGA TAC GAC GGG CGT ACT AGC GTT GGC GGG TAT AGG GTA GAG C | 22 | hexon | |
| Ad5 fiber-F2 | CGA TAC GAC GGG CGT ACT AGC GTT ATT CAG CAG CAC CTC CTT G | 23 | Adenovirus 5 | 2046 bp |
| Ad5 fiber-R2 | CGA TAC GAC GGG CGT ACT AGC GGG TGG CAG GTT GAA TAC TAG | 24 | fiber | |

TABLE 2(a)-continued

List of PCR primers in primer mix A used for multiplex PCR

| Primer name | Sequence (5'-3') | SEQ ID NO. | Organism gene | Amplicon size |
|---|---|---|---|---|
| Ad5 E1A-F3 | CGA TAC GAC GGG CGT ACT AGC GGG CTG ATA ATC TTC CAC CTC C | 25 | Adenovirus 5 E1A | 808 bp |
| Ad5 E1A-R3 | CGA TAC GAC GGG CGT ACT AGC GCT CTC ACG GCA ACT GGT TTA A | 26 | | |
| Ad4 hexon-F3 | CGA TAC GAC GGG CGT ACT AGC GGA CAG GAC GCT TCG GAG TAC | 27 | Adenovirus 4 hexon | 1334 bp |
| Ad4 hexon-R3 | CGA TAC GAC GGG CGT ACT AGC GGG CAA CAT TGG CAT AGA GGA AG | 28 | | |
| Ad4 fiber-F2 | CGA TAC GAC GGG CGT ACT AGC GGG TGG AGT GAT GGC TTC G | 29 | Adenovirus 4 fiber | 1245 bp |
| Ad4 fiber-R2 | CGA TAC GAC GGG CGT ACT AGC GAG TGC CAT CTA TGC TAT CTC C | 30 | | |
| Ad4F E1A-F1 | CGA TAC GAC GGG CGT ACT AGC GGC CGT GGA GTA AAT GGC TAA | 31 | Adenovirus 4 E1A | 1506 bp |
| Ad4F E1A-R1 | CGA TAC GAC GGG CGT ACT AGC GAG TCT TCC AAG ACC GTC CAA | 32 | | |
| Ad7 hexon-F2 | CGA TAC GAC GGG CGT ACT AGC GAT GTG ACC ACC GAC CGT AG | 33 | Adenovirus 7 hexon | 2417 bp |
| Ad7 hexon-R2 | CGA TAC GAC GGG CGT ACT AGC GGT TGC TGG AGA ACG GTA TG | 34 | | |
| Ad7 fiber-F1 | CGA TAC GAC GGG CGT ACT AGC GTC TAC CCC TAT GAA GAT GAA AGC | 35 | Adenovirus 7 fiber | 688 bp |
| Ad7 fiber-R1 | CGA TAC GAC GGG CGT ACT AGC GGG ATA GGC AGT TGT GCT GGG CAT | 36 | | |
| Ad7 E1A-F2 | CGA TAC GAC GGG CGT ACT AGC GTG AGT GCC AGC GAG AAG AG | 37 | Adenovirus 7 E1A | 786 bp |
| Ad7 E1A-R2 | CGA TAC GAC GGG CGT ACT AGC GCA GGA GGT GAG GTA GTT GAA TC | 38 | | |
| A tha TIM-F2 | CGA TAC GAC GGG CGT ACT AGC GTC AAA TCC TCG TTG ACA GAC | 39 | A. thaliana TIM | 503 bp |
| A tha TIM-R2 | CGA TAC GAC GGG CGT ACT AGC GTG CAC TGT TGC CTC CAT TGA | 40 | | |

TABLE 2(b)

List of PCR primers in primer mix B used for multiplex PCR

| Primer name | Sequence (5'-3') | SEQ ID NO. | Organism gene | Amplicon size |
|---|---|---|---|---|
| PIV I HN-F2 | CGA TAC GAC GGG CGT ACT AGC GAC AGG AAT TGG CTC AGA TAT G | 41 | Parainfluenza 1 hemagglutinin-neuraminidase | 382 bp |
| PIV I HN-R2 | CGA TAC GAC GGG CGT ACT AGC GAC ATG ATC TCC TGT TGT CGT | 42 | | |
| PIV III HV-F2 | CGA TAC GAC GGG CGT ACT AGC GTC GAG GTT GCC AGG ATA TAG G | 43 | Parainfluenza 3 hemagglutinin-neuraminidase | 477 bp |
| PIV III HN-R2 | CGA TAC GAC GGG CGT ACT AGC GGG ACT ATG AGA TGC CTG ATT GC | 44 | | |
| PIV III 5'ND-F2 | CGA TAC GAC GGG CGT ACT AGC GCA ACT ATT AGC AGT CAC ACT CG | 45 | Parainfluenza 1 5' noncoding region | 180 bp |
| PIV III 5'ND-R2 | CGA TAC GAC GGG CGT ACT AGC GAA GTT GGC ATT GTG TTC AGT G | 46 | | |
| HRhino 5'ND-F2 | CGA TAC GAC GGG CGT ACT AGC GTC ATC CAG ACT GTC AAA GG | 47 | Rhinovirus 89 5' noncoding region | 423 bp |
| HRhino 5'ND-R2 | CGA TAC GAC GGG CGT ACT AGC GAA ACA GGA AAC ACG GAC ACC | 48 | | |
| RSV Lpol-F2 | CGA TAC GAC GGG CGT ACT AGC GCT CTA TCA TCA CAG ATC TCA GC | 49 | RSV*-A L-polymerase | 388 bp |
| RSV Lpol-R2 | CGA TAC GAC GGG CGT ACT AGC GCA TGA GTC TGA CTG GTT TGC | 50 | | |
| RSVA MNN-F2 | CGA TAC GAC GGG CGT ACT AGC GAC AAA GAT GGC TCT TAG CAA AG | 51 | RSV*-A major nucleocapsid | 196 bp |
| RSVA MNN-R2 | CGA TAC GAC GGG CGT ACT AGC GAC CCA GTG AAT TTA TGA TTA GC | 52 | | |
| RSVB MNN-F2 | CGA TAC GAC GGG CGT ACT AGC GAA AAC CAA CCC AAC CAA ACC | 53 | RSV*-B major nucleocapsid | 248 bp |
| RSVB MNN-R2 | CGA TAC GAC GGG CGT ACT AGC GGC ACA TCA TAA TTG GGA GTG TC | 54 | | |
| WNVC C-F2 | CGA TAC GAC GGG CGT ACT AGC GGC TCT CTT GGC GTT CTT CAG | 55 | West Nile virus C and prM | 407 bp |
| WNVC C-R2 | CGA TAC GAC GGG CGT ACT AGC GTC ATT ACC AGC CGA CAG CAC | 56 | | |
| WNV E-F2 | CGA TAC GAC GGG CGT ACT AGC GCC GTC AGC GAT CTC TCC AC | 57 | West Nile Virus E | 107 bp |
| WNV E-R2 | CGA TAC GAC GGG CGT ACT AGC GCC TGT CCA CCA CTC CTT GTC | 58 | | |
| WNV NS1-F2 | CGA TAC GAC GGG CGT ACT AGC GTT GAA AGG GCA GTT CTG G | 59 | West Nile Virus NS1 | 150 bp |
| WNV NS1-R2 | CGA TAC GAC GGG CGT ACT AGC GCA GGT CTC CGA TTG TGA TTG C | 60 | | |
| coron229E MG-F2 | CGA TAC GAC GGG CGT ACT AGC GCT CTG GTG TGT GGT GCT TAT A | 61 | Coronavirus 229E membrane glycoprotein | 718 bp |
| coron229E MG-R2 | CGA TAC GAC GGG CGT ACT AGC GCT CGG CAC GGC AAC TGT C | 62 | | |

TABLE 2(b)-continued

List of PCR primers in primer mix B used for multiplex PCR

| Primer name | Sequence (5'-3') | SEQ ID NO. | Organism gene | Amplicon size |
|---|---|---|---|---|
| coronOC43 MG-F2 | CGA TAC GAC GGG CGT ACT AGC GAT GTG GAT GAC GTT TAG GTA | 63 | Coronavirus OC43 Membrane glycoprotein | 676 bp |
| coronOC43 MG-R2 | CGA TAC GAC GGG CGT ACT AGC GGG TTG ATG GCA GTC GGT AA | 64 | | |
| S pne lytA-F2 | CGA TAC GAC GGG CGT ACT AGC GAA GAA GAG TTC ATG ACG GAC | 65 | S. pneumoniae Autolysin | 148 bp |
| S pne lytA-R2 | CGA TAC GAC GGG CGT ACT AGC GTG GTT GTT TGG TTG GTT ATT CG | 66 | | |
| S pne ply-F2 | CGA TAC GAC GGG CGT ACT AGC GCC GAT GAC TTA TAG TAT TGA | 67 | S. pneumoniae pneumolysin | 129 bp |
| S pne ply-R2 | CGA TAC GAC GGG CGT ACT AGC GAT AAT CTT GAT GCC ACT TAG C | 68 | | |
| M pne CytP1-F2 | CGA TAC GAC GGG CGT ACT AGC GGT TCT TCA GGC TCA GGT CAA TC | 69 | M. pneumoniae Cytadhesin P1 protein | 390 bp |
| M pne CytP1-R2 | CGA TAC GAC GGG CGT ACT AGC GAC AGC GGT ATG TAC TGG TCA TA | 70 | | |
| N men ctrA-F2 | CGA TAC GAC GGG CGT ACT AGC GTG GGA ATA GTG TGC GTA TGC | 71 | N. meningitidis capsular transport protein | 195 bp |
| N men ctrA-R2 | CGA TAC GAC GGG CGT ACT AGC GAC ATC ACC GCG ACG CAG CAA | 72 | | |
| N men crag-F2 | CGA TAC GAC GGG CGT ACT AGC GGA TTC CGC GAT GCC GAT G | 73 | N. meningitidis regulatory protein, crgA | 318 bp |
| N men crag-R2 | CGA TAC GAC GGG CGT ACT AGC GCG CCC ATG TAT TTA GAG AAC CG | 74 | | |
| B per PTXP-F2 | CGA TAC GAC GGG CGT ACT AGC GCC GGC GTC GTG CGC GAA A | 75 | B. pertussis pertussis toxin promoter region | 361 bp |
| B per PTXP-R2 | CGA TAC GAC GGG CGT ACT AGC GCA GCC ACG TCA GCC AGC C | 76 | | |
| B per ptxS1-F3 | CGA TAC GAC GGG CGT ACT AGC GGA GCG AAT ATC TGG CAC ACC | 77 | B. pertussis pertussis toxin S1 subunit | 337 bp |
| B per ptxS1-R3 | CGA TAC GAC GGG CGT ACT AGC GGG GCC AGG TCT AGA ACG AAT | 78 | | |
| C pne VD4-F2 | CGA TAC GAC GGG CGT ACT AGC GTG GAG TAC AAT GGT CTC GAG C | 79 | C. pneumoniae major outer membrane protein VD4 | 161 bp |
| C pne VD4-R2 | CGA TAC GAC GGG CGT ACT AGC GTT TGC ATG AAG TCT GAG AAC GA | 80 | | |
| C pne rpoB-F2 | CGA TAC GAC GGG CGT ACT AGC GAC GGC ATT ACA ACG GCT AG | 81 | C. pneumoniae DNA directed RNA polymerase | 406 bp |
| C pne rpoB-R2 | CGA TAC GAC GGG CGT ACT AGC GCA TCT TCT GGT AAT CCC TGT TC | 82 | | |
| C pne VD2-F2 | CGA TAC GAC GGG CGT ACT AGC GAC AGC GTT CAA TCT CGT TGG | 83 | C. pneumoniae major outer membrane protein VD2 | 249 bp |
| C pne VD2-R2 | CGA TAC GAC GGG CGT ACT AGC GAG AGA ATT GCG ATA CGT TAC AG | 84 | | |
| S pyo speB-F2 | CGA TAC GAC GGG CGT ACT AGC GCC TTA CAA CCT ATT GAC ACC TG | 85 | S. pyogenes pyrogenic exotoxin B | 371 bp |
| S pyo speB-R2 | CGA TAC GAC GGG CGT ACT AGC GAC ACG AGA GCT ACC TGC AGA | 86 | | |
| S pyo mef-F2 | CGA TAC GAC GGG CGT ACT AGC GTT TAT ACA ATA TGG GCA GGG | 87 | S. pyogenes macrolide-efflux determinant (mefA, mefE) | 381 bp |
| S pyo mef-R2 | CGA TAC GAC GGG CGT ACT AGC GTC GTA AGC TGT TCT TCT GGT AC | 88 | | |
| S pyo ermB-F2 | CGA TAC GAC GGG CGT ACT AGC GTC ATT GCT TGA TGA AAC TGA T | 89 | S. pyogenes erythromycin resistance methylase (ermB) | 244 bp |
| S pyo ermB-R2 | CGA TAC GAC GGG CGT ACT AGC GTT GGA TAT TCA CCG AAC ACT AG | 90 | | |
| S pyo ermTR-F2 | CGA TAC GAC GGG CGT ACT AGC GCT TGT GGA AAT GAG TCA ACG G | 91 | S. pyogenes erm(TR) | 233 bp |
| S pyo ermTR-R2 | CGA TAC GAC GGG CGT ACT AGC GAG GTA GCT ATA TTT CGC TTG AC | 92 | | |
| B ant rpoB-F2 | CGA TAC GAC GGG CGT ACT AGC GGA GCG TCT ACG TCC TGG TGA | 93 | B. anthracis RNA polymerase beta-subunit | 291 bp |
| B ant rpoB-R2 | CGA TAC GAC GGG CGT ACT AGC GCA TTG GTT TCG CTG TTT TGA | 94 | | |
| B ant pag-F2 | CGA TAC GAC GGG CGT ACT AGC GTG GAA GAG TGA GGG TGG ATA C | 95 | B. anthracis protective antigen | 486 bp |
| B ant pag-R2 | CGA TAC GAC GGG CGT ACT AGC GAA TAA TCC CTC TGT TGA CGA A | 96 | | |

TABLE 2(b)-continued

List of PCR primers in primer mix B used for multiplex PCR

| Primer name | Sequence (5'-3') | SEQ ID NO. | Organism gene | Amplicon size |
|---|---|---|---|---|
| B ant capB-F2 | CGA TAC GAC GGG CGT ACT AGC GAG GAG CAA TGA GAA TTA CAC G | 97 | *B. anthracis* | 311 bp |
| B ant capB-R2 | CGA TAC GAC GGG CGT ACT AGC GCT AAG TTC CAA TAC TCT TGC | 98 | poly(D-glutamic acid) capsule | |
| VMVHA-F3 | CGA TAC GAC GGG CGT ACT AGC GGC CGG TAC TTA TGT ATG TGC ATT | 99 | Variola Major Virus | 439 bp |
| VMVHA-R3 | CGA TAC GAC GGG CGT ACT AGC GCA TCA TTG GCG GTT GAT TTA | 100 | hemagglutinin | |
| VMVcrmB-F3 | CGA TAC GAC GGG CGT ACT AGC GGG GAA CAT ACG CTT CCA GAT | 101 | Variola Major Virus | 257 bp |
| VMVcrmB-R3 | CGA TAC GAC GGG CGT ACT AGC GTT CCA CAT TTT GTT TGG GAA A | 102 | cytokine response modifier B | |
| EVLGV-F3 | CGA TAC GAC GGG CGT ACT AGC GCC TTA TCC GAC TCG CAA TGT | 103 | Ebola Virus | 366 bp |
| EVLGV-R3 | CGA TAC GAC GGG CGT ACT AGC GCA GTG TGA GGT TAT GTG GTG GA | 104 | L gene | |
| LVGPC-F4 | CGA TAC GAC GGG CGT ACT AGC GTT GGT TGC GCA ATT CAA GT | 105 | Lassa Virus | 302 bp |
| LVGPC-R4 | CGA TAC GAC GGG CGT ACT AGC GTG TTG TTC TTT GTG CAG GAG A | 106 | GPC gene | |
| F tul 13Kd-F2 | CGA TAC GAC GGG CGT ACT AGC GTC GTA ATG TTA GCT GTA TCA TC | 107 | *F. tularensis* | 513 bp |
| F tul 13Kd-R2 | CGA TAC GAC GGG CGT ACT AGC GTA CAT TAG CTG TCC ACT TAC CG | 108 | 13-kDa lipoprotein | |
| F tul FopA-F2 | CGA TAC GAC GGG CGT ACT AGC GGT GGG TGG TGG TCT TAA GTT T | 109 | *F. tularensis* | 192 bp |
| F tul FopA-R2 | CGA TAC GAC GGG CGT ACT AGC GCT GGA TAT TAC CAG TGT CAT T | 110 | FopA | |
| Y pes cve-F2 | CGA TAC GAC GGG CGT ACT AGC GAC TGA TAA AGG GGA GTG GAT A | 111 | *Y. pestis* | 388 bp |
| Y pes cve-R2 | CGA TAC GAC GGG CGT ACT AGC GCT CGC CTT GCT CTT TGA GC | 112 | cve2155 sequence | |
| Y pes caf1-F2 | CGA TAC GAC GGG CGT ACT AGC GGG ACA CAA GCC CTC TCT ACG | 113 | *Y. pestis* | 564 bp |
| Y pes caf1-R2 | CGA TAC GAC GGG CGT ACT AGC GTA GAT ACG GTT ACG GTT ACA G | 114 | Caf1 | |
| AthaNAC1-F5 | CGA TAC GAC GGG CGT ACT AGC GCA TGG GAA GCT GTT TTG ATG | 115 | *A. thaliana* | 497 bp |
| AthaNAC1-R5 | CGA TAC GAC GGG CGT ACT AGC GCC CGA AGA ATT GTT CCA ATC | 116 | NAC1 | |

*RSV: Respiratory syncytial virus

The RT reaction products were split up into two 10 μl volumes to be subjected to two different multiplex PCR reactions. Primer mix A contained 19 primer pairs and amplifies 18 gene targets from 3 different influenza A viruses, 1 influenza B virus, 3 serotypes of HAdVs, and one internal control (TIM). Primer mix B contains 38 primer pairs and amplifies the remaining 37 gene targets and the other internal control (NAC1). PCR reactions were performed in 50 μl volumes containing 20 mM Tris-HCl (pH 8.4), 50 mM KCl, 2 mM $MgCl_2$, 400 μM each of dATP, dCTP, dGTP, dUTP, 1 U of Uracil-DNA glycosylase, heat-labile (USB, Carlsbad, Calif.), 2 μM of primer L, 40 nM each of primers from mix A or 50 nM each of primers from mix B, 10 U of Platinum Taq DNA polymerase (Invitrogen Life Technologies, Carlsbad, Calif.), and 10 μl of RT product. The amplification reaction was carried out in Peltier Thermal Cycler-PTC240 DNA Engine Tetrad 2 (MJ Research Inc., Reno, Nev.) with initial incubation at 25° C. for 10 min., preliminary denaturation at 94° C. for 3 min., followed by 5 cycles of: 94° C. for 30 sec., 50° C. for 90 sec., 72° C. for 120 sec., then 35 cycles of: 94° C. for 30 sec., 64° C. for 120 sec., and a final extension at 72° C. for 5 min. The amplified products from both PCR reactions were combined into a single volume and subjected to purification and processing prior to hybridizing to the RPM v.1 chips (see below).

Example 6

Microarray hybridization and processing—The two PCR product mixtures were recombined after amplification for fragmentation and hybridization to the microarray. Microarray hybridization and processing were carried out according to the manufacturer's recommended protocol (Affymetrix Inc., Santa Clara, Calif.) with the following modification. Purified PCR products were fragmented at 37° C. for 5 minutes, and then labeled with Biotin-N-6-ddATP at 37° C. for 30 minutes. Hybridization was carried out in a rotisserie oven at 45° C. and 60 rev/min for 2 hours. After scanning, the GCOS software was used to reduce the raw image (.DAT) file to a simplified file format (.CEL file) with intensities assigned to each of the corresponding probe positions. Finally, the GDAS software was used to apply an embedded version of the ABACUS (Cutler et al., "High-throughput variation detection and genotyping using microarrays" *Genome Res.,* 11, 1913-1925 (2001)) algorithm to produce an estimate of the correct base calls, comparing the respective intensities for the sense and anti-sense probe sets. To increase the percentage of base calls, the parameters were adjusted to allow the most permissive base calling (shown below). The sequences from base calls made for each tiled region of the resequencing array then were exported from GDAS as FASTA-formatted files.

Filter Conditions
   No Signal threshold=0.500 (default=1.000000)
   Weak Signal Fold threshold=20000.000 (default=20.000000)
   Large SNR threshold=20.000000 (default=20.000000)
Algorithm Parameters
   Strand Quality Threshold=0.000 (default=0.000000)
   Total Quality Threshold=25.0000 (default=75.000000)
   Maximum Fraction of Heterozygote Calls=0.99000 (default=0.900000)
   Model Type (0=Heterozygote, 1=Homozygote)=0
   Perfect Call Quality Threshold=0.500 (default=2.000000)
Final Reliability Rules
   Min Fraction of Calls in Neighboring Probes=1.0000 (disables filter)
   Min Fraction of Calls of Samples=1.0000 (disables filter)

Example 7

Automatic Pathogen Identification Algorithm (Pathogen Identification based on NA sequence)—The raw output sequences generated from microarray hybridization and scanning were processed using an algorithm that identifies pathogens using sequence similarity comparisons against database records. A new software program, Computer-Implemented Biological Sequence-based Identifier system version 2 (CIBSI 2.0) was developed to analyze the results completely by incorporating in the tasks performed previously in the Resequencing Pathogen Identification (REPI) program (Lin et al., "Broad-spectrum respiratory tract pathogen identification using resequencing DNA microarrays" *Genome Res.*, 16(4), 527-535 (2006)), and in addition performing decisions that were previously done manually. A broader discussion of this protocol, including an improved REPI algorithm is described in detail in U.S. patent application Ser. No. 11/422,431.

Example 8

Quantification of pathogens—The specificity of this assay was confirmed using various prototype strains and clinical samples. The results showed no discernible interference between targets. The analytical sensitivity of the RPM v.1 assay was then evaluated using serial ten-fold dilutions of the nucleic acid templates of the prototype strains. Table 1 shows the lowest dilution for each pathogen to which that pathogen was detectable. The results revealed a sensitivity range from 10 to $10^3$ genomic copies per reaction for the prototype strains, which is comparable to the sensitivity of standard multiplex RT-PCR/PCR methods. It should be noted that genome copy number should not be equated to viable count (plaque forming units), as genome copy number is usually at least one, if not several orders of magnitude higher than viable count for respiratory pathogens. The capability of RPM v.1 to identify and discriminate between near genetic neighbors that was first demonstrated with more specific protocols has been reproduced with this protocol. The sequences generated from 17 different serotypes of human adenovirus (HAdV) revealed that this assay could differentiate various ARI-associated HAdV strains and proved that this assay could be used for detecting a broad range of variants (Table 3). Cross hybridization of targets was observed on only HAdV hexon genes among different serotypes; but this does not interfere with positive identification of the correct targeted pathogens.

TABLE 3

Differentiation of various FRI-causing HAdVs with RPM v.1.

| Sample | Strains | Strain identification by RPM v.1 |
|---|---|---|
| HAdV-4 | RI-67 | HAdV-4 (AY594253) |
| HAdV-4 vaccine | CL68578 | HAdV-4 vaccine (AY594254) |
| HAdV-4FS_Navy | | HAdV-4FS_Navy (AY599835) |
| HAdV-4FS_AirForce | | HAdV-4FS_AirForce (AY599837) |
| HAdV-5 | adenoid 75 | HAdV-5 (AY339865) |
| HAdV-1 | adenoid 71 | HAdV-1 (AY490817) |
| HAdV-2 | adenoid 6 | HAdV-2 (J01917) |
| HAdV-6 | tonsil 99 | HAdV-6 (DQ149613) |
| HAdV-7 | Gomen | HAdV-7 (AY594255) |
| HAdV-7a vaccine | 55142 | HAdV-7 (AY 594256) |
| HAdV-7FS_Navy | | HAdV-7FS_Navy (AY601634) |
| HAdV-3 | GB | HAdV-3 (DQ086466) |
| HAdV-3FS_Navy | | HAdV-3 US Navy Field Strain (AY 599836) |
| HAdV-16 | Ch. 79 | HAdV-16 (AY601636) |
| HAdV-21 | AV-1645 [128] | HAdV-21 (AF492353) |
| HAdV-11 | Slobitski | HAdV-11 (AY598970) |
| HAdV-14 | De Wit | HAdV-14 (AY803294) |

For sensitivity assessments, real-time PCR assays were conducted on iCycler or MYIQ™ instruments (Bio-Rad Laboratories, Hercules, Calif.) to determine the number of adenovirus genomes in each sample. The findings for the samples were compared to those for ten-fold serial dilution of HAdV-4 prototype genomic DNA templates of known copy number ($10^1$ to $10^6$ copies) by using fiber specific primers Ad4F-F and Ad4F-R (Table 4). HAdV-4 genomic copy number was calculated by measuring DNA concentration from purified viral DNA and using the following conversion factor: 0.384 fg=a single adenoviral genome of ~35 kb. Real-time PCR reactions were carried out in 25 µl reaction volumes containing 2.5 µl FastStart Reaction Mix SYBR Green I (Roche Applied Science, Indianapolis, Ind.), 20 mM Tris-HCl (pH 8.4), 50 mM KCl, 3 mM $MgCl_2$, 200 µM each of dATP, dTTP, dGTP, dCTP, 200 nM primers, and adenoviral genomic DNA (1-4 µl of clinical specimen or DNA extracts). The amplification reaction was carried out with preliminary denaturation at 94° C. for 10 min. followed by 40 cycles of: 94° C. for 20 sec., 60° C. for 30 sec.

Similar assays were carried out to determine the genomic copy number of other pathogens by using specific primers (Table 4) and RT-PCR/PCR conditions as previously described (Stone et al., "Rapid detection and simultaneous subtype differentiation of influenza A viruses by real time PCR" *J. Virol. Methods,* 117, 103-112 (2004); Hardegger et al., "Rapid detection of *Mycoplasma pneumoniae* in clinical samples by real-time PCR" *J. Microbiol. Methods,* 41, 45-51 (2000); Corless et al., "Simultaneous detection of *Neisseria meningitidis, Haemophilus influenzae,* and *Streptococcus pneumoniae* in suspected cases of meningitis and septicemia using real-time PCR" *J. Clin. Microbiol.,* 39, 1553-1558 (2001); Mölling et al., "Direct and rapid identification and genogrouping of meningococci and porA amplification by LightCycler PCR" *J. Clin. Microbiol.,* 40, 4531-4535 (2002); Vabret et al., "Direct diagnosis of human respiratory coronaviruses 229E and OC43 by the polymerase chain reaction" *J. Virol. Methods,* 97, 59-66 (2001)).

TABLE 4

List of PCR primers used for quantitative real-time PCR

| Primer name | Sequence (5'-3') | SEQ ID NO. | Organism gene | Amplicon size | Accession no. Reference |
|---|---|---|---|---|---|
| AMPfor1 | GAC CAA TCC TGT CAC CTC TGA | 117 | Influenza A matrix | 229 | AF138708 Stone et al. 2004 |
| AMPrev1 | GTA TAT GAG KCC CAT RCA ACT | 118 | | | |
| BMA-F1 | TCG GTG GGA AAG AAT TTG AC | 119 | Influenza B matrix | 162 | AF100378 This study |
| BMA-R1 | TTC CTG ATA GGG GCT CTG TG | 120 | | | |
| Ad4F-F | ACA AGC AAG GAG ATA GCA TAG ATG | 121 | Human Adenovirus 4 fiber | 281 | X76547 This study |
| Ad4F-R | GTA GGA GAA GGT GTA TGA GTT AGC | 122 | | | |
| C229E-MG-F1 | ACC TGG GCT AAT TGG GAT TC | 123 | Coronavirus 229E membrane glycoprotein | 222 | AF304460 This study |
| C229E-MG-R1 | AAT GCC TGT TGG AGC TTG TT | 124 | | | |
| COC43-MG-F1 | GGC TTA TGT GGC CCC TTA CT | 125 | Coronavirus OC43 membrane glycoprotein | 284 | M93390 Vabret et al., 2001 |
| COC43-MG-R1 | AAG ATG GCC GCG TAT TAT TG | 126 | | | |
| PIV1-HN-F2 | GGC TCA GAT ATG CGA GAA CA | 127 | Parainfluenza 1 hemagglutinin-neuraminidase | 140 | U70948 This study |
| PIV-HN-R2 | TTG GTC CGG GTA ATA ATG AGA | 128 | | | |
| PIV3-HN-F2 | CCA TAT GCG GCA TTA TAC CC | 129 | Parainfluenza 3 hemagglutinin-neuraminidase | 150 | M20402 This study |
| PIV3-HN-R2 | GCA GTC TCT CTG CGT TTT CC | 130 | | | |
| Rhino-5'-F1 | TGC TTT ACC CAA GGC AAA AA | 131 | Rhinovirus 89 5' noncoding region | 130 | NC_001617 This study |
| Rhino-5'-R1 | AGC CTC ATC TGC CAG GTC TA | 132 | | | |
| RSVA-N-F2 | AAG ATG GCT CTT AGC AAA GTC AA | 133 | RSV*-A major nucleocapsid | 100 | M11486 This study |
| RSVA-N-R2 | TAC TAT CTC CTG TGC TCC GTT G | 134 | | | |
| RSVB-N-F2 | TGG GGC AAA TAC AAA GAT GG | 135 | RSV*-B major nucleocapsid | 136 | AF013254 This study |
| RSVB-N-R2 | CAC ATC ATA ATT GGG AGT GTC AA | 136 | | | |
| PI549 | CCA ACC AAA CAA CAA CGT TCA | 137 | M. pneumoniae P1 adhesion protein | 76 | X07191 Hardegger et al., 2000 |
| PI624 | ACC TTG ACT GGA GGC CGT TA | 138 | | | |
| PI572@ | TCA ACT CGA ATA ACG GTG ACT TCT TAC CAC TG | 139 | | | |
| ply894 | TGC AGA GCG TCC TTT GGT CTA T | 140 | S. pneumoniae pneumolysin | 81 | M17717 Corless et al., 2001 |
| ply974 | CTC TTA CTC GTG GTT TCC AAC TTG A | 141 | | | |
| ply941@ | TGG CGC CCA TAA GCA ACA CTC GAA | 142 | | | |
| RS-F1 | AAC AGA TGT AAG CAG CTC CGT TAT C | 143 | RSV Fusion protein | 65 | AF067125 Mentel et al. 2003 |
| RS-F2 | CGA TTT TTA TTG GAT GCT GTA CAT TT | 144 | | | |
| RS-F3@ | TGC CAT AGC ATG ACA CAA TGG CTC CT | 145 | | | |
| porA-F2 | CGG CAG CGT (C/T) CA ATT CGT TC | 146 | N. meningitidis PorA (Porin) | 309 | AF239810 Mölling et al. 2002 |
| porA-R2 | CAA GCC GCC TTC CTC ATA GC | 147 | | | |

*RSV: Respiratory syncytial virus, @Dual-labeled probe contains 6-carboxy-fluorescein (FAM) as the fluores-reporter dye at the 5' end, and the Black Hole Quenchers at the 3' end.
Acession references:
Stone et al., "Rapid detection and simultaneous subtype differentiation of influenza A viruses by real time PCR" J. Virol. Methods, 117, 103-112 (2004).
Vabret et al., "Direct diagnosis of human respiratory coronaviruses 229E and OC43 by the polymerase chain reaction" J. Virol. Methods, 97, 59-66 (2001)
Hardegger et al., "Rapid detection of Mycoplasma pneumoniae in clinical samples by real-time PCR" J. Microbiol. Methods, 41, 45-51 (2000)
Corless et al., "Simultaneous detection of Neisseria meningitidis, Haemophilus influenzae, and Streptococcus pneumoniae in suspected cases of meningitis and septicemia using real-time PCR" J. Clin. Microbiol., 39, 1553-1558 (2001)
Mentel et al., "Real-time PCR to improve the diagnosis of respiratory syncytial virus infection" J. Med. Microbiol., 52, 893-896 (2003)
Mölling et al., "Direct and rapid identification and genogrouping of meningococci and porA amplification by LightCycler PCR" J. Clin. Microbiol., 40, 4531-4535 (2002)

Example 9

Simultaneous detection and differentiation of respiratory pathogens—Previous studies have shown that, in addition to accurately identifying single pathogenic species, one of the salient benefits of using the RPM v.1 assay for pathogen detection is the ability to detect co-infections. In this study, the ability of the RPM v.1 assay to identify multiple pathogens simultaneously was further assessed by the preparation of various combinations of pathogen templates (Table 5 and 6). Serial dilutions of the template were used to evaluate the detection sensitivity and specificity for multiple pathogens. Nucleic acid templates containing $10^6$-$10^3$ genome copies per reaction of each pathogen, HAdV-4, *S. pyogenes*, *M. pneumoniae*, and *Y. pestis* were mixed together and tested with RPM v.1 arrays. These results demonstrated that this assay allows reproducible sequence-based identification of all 4 pathogens even at the lowest concentration of $10^3$ genomic copies per target per reaction (Table 5). The fact that there was no discernible interference in this complex mix further supported the robustness of the nucleotide base calling capability of the RA and the attendant identification algorithms, even in complex mixtures.

To further evaluate the effectiveness of this approach for multiple pathogen detection in a complex mixture, 3-7 cultured organisms were spiked at different titers [$10^2$-$10^5$ (cfu or pfu)/mL] into pooled nasal wash collected from volunteers, and 150 μL of the prepared samples were used for testing. Initial results revealed that this approach allowed unambiguous detection of 7 pathogens, HAdV-4, HAdV-7, *B. anthracis*, Influenza A-H1N1, Parainfluenza virus 1, RSV-A, *M. pneumoniae*, and *S. pyogenes* simultaneously at the lowest titer-100 cfu (pfu)/mL (Table 6). Further assessment with a different set of 7 pathogens showed that the RPM v.1 assay could simultaneously detect 6 of them. Among these, HAdV-4, *B. anthracis*, Influenza A-H1N1, RSV-A, and *M. pneumoniae* were detected at the lowest titer-100 cfu (pfu)/mL, and *S. pyogenes* was detected at 1000 cfu/mL (Table 6). *Y. pestis* could not be detected even at the highest concentrations. This was attributed to an inadequacies of the nucleic acid extraction protocol for the intact *Y. pestis* pathogen, since 1000 genome copies of *Y. pestis* could be detected when purified nucleic acid templates were used (Tables 1 and 5). For further confirmation, the RPM v.1 was tested with cultured organisms on same set of 4 pathogens that were tested using purified nucleic acid template (Table 5). Without failure, the results showed that the assay could reproducibly detect HAdV-4 and *M. pneumoniae* at 100 cfu (pfu)/mL, with less sensitivity for *S. pyogenes* (1000 cfu/mL) but not *Y. pestis*. When testing three pathogens simultaneously, in this case *B. anthracis*, Influenza A-H1N1, and HCoV-229E or RSV-A, the assay detected all three pathogens at titers as low as 100 cfu (pfu)/mL (Table 6). These results indicate that the RA-based approach is an effective means of detecting and typing various pathogens directly from nasal wash samples with the benefit of high sensitivity and specificity for detecting co-infections of at least 7 pathogens. This approach will be useful for routine diagnosis and epidemic survey of these pathogens within the population, providing new information on the incidence of multiple pathogens.

TABLE 5

Simultaneous detection of multiple nucleic acid templates by RPM v.1

| Genome copies | HAdV-4 | GAS | MP | YP |
|---|---|---|---|---|
| $10^6$ | + | + | + | + |
| $10^5$ | + | + | + | + |
| $10^4$ | + | + | + | + |
| $10^3$ | + | + | + | + |

Note:

Sample was generated by mixing purified nucleic acid templates in TE buffer to create $10^6$ genome copies/ul stock solution. Starting from this concentration, 10-fold serial dilutions in TE buffer were prepared.

TABLE 6

Simultaneous detection of multiple pathogens by RPM v.1

| Titer | HAdV-4 | GAS | MP | H1N1 | RSV-A | HAdV-7 | PIV1 |
|---|---|---|---|---|---|---|---|
| $10^5$ | + | + | + | + | + | + | + |
| $10^4$ | + | + | + | + | + | + | + |
| $10^3$ | + | + | + | + | + | + | + |
| $10^2$ | + | + | + | + | + | + | + |

| Titer | HAdV-4 | GAS | MP | H1N1 | RSV-A | BA | YP |
|---|---|---|---|---|---|---|---|
| $10^5$ | + | + | + | + | + | + | − |
| $10^4$ | + | + | + | + | + | + | − |
| $10^3$ | + | + | + | + | + | + | − |
| $10^2$ | + | + | + | + | + | + | − |

| Titer | HAdV-4 | GAS | MP | YP |
|---|---|---|---|---|
| $10^5$ | + | + | + | − |
| $10^4$ | + | + | + | − |
| $10^3$ | + | + | + | − |
| $10^2$ | + | − | + | − |

| Titer | BA | H1N1 | HCoV-229E |
|---|---|---|---|
| $10^5$ | + | + | + |
| $10^4$ | + | + | + |
| $10^3$ | + | + | + |
| $10^2$ | + | + | + |

| Titer | BA | H1N1 | RSV-A |
|---|---|---|---|
| $10^5$ | + | + | + |
| $10^4$ | + | + | + |
| $10^3$ | + | + | + |
| $10^2$ | + | + | + |

Note:

Samples were generated by mixing culture samples with pooled nasal washes collected from normal volunteers to generate $10^5$ cfu(pfu)/ml. Starting from this concentration, 10-fold serial dilution with pooled nasal washes collected from normal volunteers was prepared. For each dilution, 150 μl of samples were used for the RPM v.1 process.
BA—*B. anthracis* (Sterne),
H1N1—influenza A-H1N1,
HCoV229E—Human coronavirus 229E,
HAdV—Human adenovirus,
GAS—*S. pyogenes* (group A *Streptococcus* ),
MP—*M. pneumoniae*,
PIV1: parainfluenza virus 1,
RSV—respiratory syncytial virus,
YP—*Y. pestis*.
+: detected,
−: not detected.

Example 10

Assessment of clinical specimens—After successfully demonstrating the capability of RPM v.1 assay for pathogen detection, it was used for prospective and the retrospective diagnoses of infections causing ARM. Clinical specimens, collected primarily from military recruits presenting with ARI, were used to compare the utility of the microarray-based diagnostic to more established methods of respiratory pathogen detection. The samples (n=101) consisted of throat swabs in viral transport medium with clinically documented respiratory illness. Samples were chosen randomly from sets that had tested positive for HAdV or influenza virus using CAP-certified diagnostic methods (cell culture and/or PCR) at NHRC. These were blinded (randomly renumbered and separated from the associated clinical records) and sent to the Naval Research Laboratory (NRL) for RPM v.1 testing. The compared experiments were conducted by two independent laboratories and the sample identities were revealed only after the results had been finalized. For influenza A virus, the RPM v.1 method showed a detection sensitivity of 87% and a specificity of 96% with respect to the initial diagnostic result, and an overall agreement of 92% (Table 7). For adenovirus, the RPM v.1 detection sensitivity was 97% with 97% specificity, for an overall agreement of 97% (Table 7). Upon further comparison of the RPM v.1 results with culture and PCR methods, the data showed comparable detection sensitivity and specificity to either culture or PCR assay (Table 8). The data suggested that the RPM v.1 had better sensitivity and specificity than culture vs. PCR, as might be expected since molecular methods are generally more sensitive than culture, and sequencing capability of the RPM v.1 method provided higher specificity than PCR (Table 9). This data further strongly demonstrated the ability of the microarray-based diagnostic to correctly identify clinically relevant influenza A virus strains in uncultured patient specimens.

TABLE 7

Evaluation of the RPM v.1 for Adenovirus, influenza A virus and negative control detection in clinical samples

| | Adenovirus | | Influenza A | |
|---|---|---|---|---|
| | PCR ©+ | PCR ©− | Culture+ | Culture− |
| RPM v.1+ | 32 | 2* | 39 | 2 |
| RPM v.1− | 1 | 66 | 6ᵋ | 54 |
| Sensitivity | 97% | | 87% | |
| Specificity | 97% | | 96% | |
| Clinical agreement | 97% | | 92% | |

©CAP-certified PCR;

*One of the CAP-certified PCR negative samples was cultured for influenza A virus, RPM v.1 showed HAdV-4 and influenza A co-infection, the other negative sample was confirmed to have low titer HAdV-4;

ᵋ3 influenza A culture positive samples could not be detected by quantitative real-time PCR as well, indicated that templates were degraded.

TABLE 8

Comparison of the RPM v.1 for influenza A virus positive and negative control detection in 40 clinical samples with culture and real-time PCR assays.

| | Influenza A | | Influenza A | |
|---|---|---|---|---|
| | Culture+ | Culture− | PCR+ | PCR− |
| RPM v.1+ | 22 | 1 | 21 | 2 |
| RPM v.1− | 3* | 14 | 2 | 15 |
| Sensitivity | 88% | | 91% | |
| Specificity | 93% | | 88% | |
| Clinical agreement | 90% | | 90% | |

TABLE 9

Comparison of the culture method for influenza A virus positive and negative control detection in 40 clinical samples with real-time PCR assay.

| | Influenza A | |
|---|---|---|
| | Culture+ | Culture− |
| PCR+ | 21 | 2 |
| PCR− | 4 | 13 |
| Sensitivity | 84% | |
| Specificity | 87% | |
| Clinical agreement | 85% | |

This study demonstrated the capability of this assay to identify the subtype of the influenza viruses and track genetic changes within influenza strains. This is especially critical for influenza epidemiology since antigenic drift is the mechanism by which influenza viruses escape from immunological pressure induced by previous natural exposures and vaccination. Analysis of hemagglutinin (HA) and neuramindase (NA) sequences generated from RPM v.1, recapitulated the known lineage changes occurring from 1999-2005 through antigenic drifting (Table 10). Seven influenza A/H3N2 clinical specimens collected prior to 2003-2004 influenza seasons were identified as belonging to the A/Panama/2007/99-like lineage, while 9 influenza A/H3N2 samples collected in 2003-2004 influenza season were clearly carrying signature A/Fujian/411/2002-like lineage nucleotide substitutions in the HA gene. The shift from an A/Fujian/411/2002-like strain to an A/California/7/2004-like strain is evident in the 18 influenza A/H3N2 samples collected in 2004-2005 influenza season. Three samples were identified as A/Fujian/411/2002-like strains while the rest showed signature California-like nucleic acid substitution in the HA gene. Two samples collected during the same period could only be identified as influenza A/H3N2. This was due to poor amplification and/or hybridization of targets, resulting in insufficient sequence information for strain level identification. Two influenza A/H1N1 samples collected in 2000-2001 were identified as closely related to A/New Caledonia/20/99.

TABLE 10

Influenza strain and lineage identification using RPM v.1

| Sample ID | Collection Date | Representative Strain Identification (Accession no. of HA gene) | Lineage |
|---|---|---|---|
| 10499 | 30 Sep 1999 | A/Charlottesville/10/99 (H3N2) (AF297094) | A/Panama/2007/99 |
| 41394 | 5 Jan 200 | A/Sydney/5/97(H3N2) (AF180584) | A/Panama/2007/99 |
| 10552 | 11 Jan 200 | A/France/2/00(H3N2) (AY633997) | A/Panama/2007/99 |
| 30491 | 13 Jan 200 | A/New York/397/1999(H3N2) (CY006163) | A/Panama/2007/99 |
| 39002 | 12 Jan 2001 | A/Podgorica/4011/2001(H1N1) (AJ457863) | A/New Caledonia/20/99 |
| 70246 | 5 Feb 2001 | A/Madrid/1082/2001(H1N1) (AJ457886)* | A/New Caledonia/20/99 |
| 50833 | 24 Jan 2002 | A/New York/110/2002(H3N2) (CY000113) | A/Panama/2007/99 |
| 61596 | 2 Feb 2002 | A/Buenos Aires/722/01(H3N2) (AF534056) | A/Panama/2007/99 |
| 20694 | 7 Mar 2002 | A/New York/101/2002(H3N2) (CY001104)* | A/Panama/2007/99 |
| 31844 | 12 Nov 2003 | A/New York/41/2003(H3N2) (CY000153)* | A/Fujian/411/2002 |
| 70793 | 21 Nov 2003 | A/New York/18/2003(H3N2) (CY001061)* | A/Fujian/411/2002 |
| 51672 | 1 Dec 2003 | A/New York/28/2003(H3N2) (CY000009) | A/Fujian/411/2002 |
| 43269 | 1 Dec 2003 | A/New York/28/2003(H3N2) (CY000009)* | A/Fujian/411/2002 |
| 51673 | 1 Dec 2003 | A/New York/43/2003(H3N2) (CY000169)* | A/Fujian/411/2002 |
| 62416 | 16 Dec 2003 | A/New York/51/2003(H3N2) (CY001064)* | A/Fujian/411/2002 |
| 90781 | 17 Dec 2003 | A/New York/41/2003(H3N2) (CY000153)* | A/Fujian/411/2002 |
| 48930 | 12 Jan 2004 | A/Finland/305/2003 (H3N2) (DQ167271) | A/Fujian/411/2002 |
| 48934 | 13 Jan 2004 | A/New York/34/2003(H3N2) (CY0000431) | A/Fujian/411/2002 |
| 32323 | 18 Jan 2005 | A/Cheju/311/2002(H3N2) (AY589649) | A/Fujian/411/2002 |
| 32327 | 20 Jan 2005 | A/New York/464/2005(H3N2) (CY003648) | A/California/7/2004 |
| 49370 | 24 Jan 2005 | A/New York/378/2005(H3N2) (CY002016) | A/California/7/2004 |
| 52067 | 05 Jan 2005 | A/New York/244/2005(H3N2) (CY002080)* | A/California/7/2004 |
| 32329 | 21 Jan 2005 | A/New York/386/2004(H3N2) (CY002040) | A/California/7/2004 |
| 49369 | 22 Jan 2005 | A/New York/387/2004(H3N2) (CY002048) | A/California/7/2004 |
| 49376 | 1 Feb 2005 | A/New York/461/2005(H3N2) (CY006076) | A/California/7/2004 |
| 49377 | 02 Feb 2005 | A/New York/372/2004(H3N2) (CY002224)* | A/California/7/2004 |
| 49378 | 02 Feb 2005 | A/New York/359/2005(H3N2) (CY002000) | A/California/7/2004 |
| 62818 | 03 Feb 2005 | A/New York/359/2005(H3N2) (CY002000) | A/California/7/2004 |
| 52082 | 05 Feb 2005 | A/H3N2 | N.D. |
| 32349 | 14 Feb 2005 | A/New York/379/2004(H3N2) (CY002026)* | A/California/7/2004 |
| 52087 | 15 Feb 2005 | A/Aichi/143/2005(H3N2) (AB243872) | A/California/7/2004 |
| 52089 | 16 Feb 2005 | A/New York/396/2005(H3N2) (CY002072) | A/California/7/2004 |
| 49417 | 24 Feb 2005 | A/New York/373/2005(H3N2) (CY002456)* | A/California/7/2004 |
| 52095 | 25 Feb 2005 | A/Finland/170/03(H3N2) (AY661032) | A/Fujian/411/2002 |
| 52096 | 26 Feb 2005 | A/Finland/170/03(H3N2) (AY661032) | A/Fujian/411/2002 |
| 52099 | 28 Feb 2005 | A/Canterbury/67/2005(H3N2) (CY008059) | A/California/7/2004 |
| 49428 | 28 Feb 2005 | A/New York/382/2005(H3N2) (CY002032)* | A/California/7/2004 |
| 49432 | 01 Mar 2005 | A/New York/373/2005(H3N2) (CY002456)* | A/California/7/2004 |
| 49449 | 07 Mar 2005 | A/H3N2 | N.D. |

Note:
*indicates only single strain was identified.

In addition to detecting single pathogens in the clinical samples, various co-infections such as HAdV-4/influenza A virus, HAdV-4/*S. pyogenes*, and influenza A virus/*M. pneumoniae* could be detected in clinical samples (data not shown). These co-infections were further verified using published type-specific PCR assays (Stone et al., "Rapid detection and simultaneous subtype differentiation of influenza A viruses by real time PCR" *J. Virol. Methods*, 117, 103-112 (2004); Hardegger et al., "Rapid detection of *Mycoplasma pneumoniae* in clinical samples by real-time PCR" *J. Microbiol. Methods*, 41, 45-5 (2000)) and in-house specific PCR primers (Table 4) (data not shown). Furthermore, the assay also detected *S. pneumoniae* in 26% and *N. meningitidis* in 16% of the clinical samples. The presence of *S. pneumoniae*, and *N. meningitidis* was verified by published species-specific quantitative real-time PCR assays (data not shown) in a subset of 40 of the clinical samples (limited due to the available volume of samples). It is well known that *S. pneumoniae*, and *N. meningitidis* are commensal bacteria in the mouth and upper respiratory system, so it is not surprising that these were commonly found in clinical samples. However, quantitative real-time PCR data showed that while most of the *S. pneumoniae* and *N. meningitidis* present in clinical samples was of low titer ($\leq 10^3$ genome copies/μl), 32% of the influenza-positive samples harbored a high titer of *S. pneumoniae* (7/25) or *N. meningitidis* (1/25) ($\geq 10^5$ genome copies/μL) (data not shown). The high titer bacteria present in these clinical samples is probably due to virally induced bacterial superinfection.

Example 11

Multiplex PCR Protocol with Primer L and LN—The following is a detailed protocol of example procedures.

Preparation Work

1. Prepare TIM RNA from pSP64poly(A)-TIM—MEGASCRIPT® SP6 kit (Ambion, Cat #1330)
    a) Linearized 1 μg of pSP64poly(A)-TIM with EcoRI enzymes

| | |
|---|---|
| x μl | pSP64poly(A)-TIM |
| 2 μl | 10X EcoRI buffer |
| 2 μl | EcoRI (NEB, Cat # R0101S) |
| (16 − x) μl | H$_2$O |
| 20 μl | Total volume |

Incubate the reaction at 37° C. for 5 hours.

b) Terminate the restriction digest by adding the following:
- ¹⁄₂₀th volume 0.5 M EDTA (1 µl)
- ¹⁄₁₀th volume of 3 M Na acetate (2 µl)
- 2 volumes of ethanol (40 µl)

c) Mix well and chill at −20° C. for 20 min. Then pellet the DNA for 15 min in a microcentrifuge at top speed.

d) Remove the supernatant, re-spin the tube for a few seconds, and remove the residual fluid with a very fine-tipped pipet. Resuspend in 20 µl Nuclease Free water.

e) Place the RNA Polymerase Enzyme Mix on ice f) Vortex the 10× Reaction Buffer and the 4 ribonucleotide solutions g) (ATP, CTP, GTP, and UTP) until they are completely in solution.

h) Once thawed, store the ribonucleotides on ice, but keep the 10× Reaction Buffer at room temperature while assembling the reaction.

i) All reagents should be microfuged briefly before opening to prevent loss and/or contamination of material that may be present around the rim of the tube.

j) Assemble the following transcription reaction at room temperature.

| | |
|---|---|
| 16 µl | Linearlized pSP64poly(A)-TIM |
| 16 µl | NTPs (ATP, GTP, CTP, UTP-4 µl each) |
| 4 µl | 10X Reaction Buffer |
| 4 µl | Enzyme Mix |
| 40 µl | Total volume |

Incubate the reaction at 37° C. for 6 hours.

k) Purify the RNA product with ProbeQuant™ G-50 Micro Column (Amersham, Cat #27533501)

l) Measure O.D. of the recovered RNA and dilute to make 60 fg/µl stock.

2. Prepare NAC1 DNA fragment from pSP64poly(A)-NAC1—PCR with platinum Taq DNA polymerase (Invitrogen, Cat #10966-034)

| | |
|---|---|
| 1 µl | pSP64poly(A)-NAC1 (1 ng/µl) |
| 5 µl | 10X PCR buffer |
| 2 µl | 50 mM MgCl₂ |
| 1 µl | 10 mM dNTP mix |
| 1 µl | SP6 (10 µM) 5'-ATT TAG GTG ACA CTA TAG AAT-3' |
| 1 µl | SP6 (10 µM) 5'-CAG GAA ACA GCT ATG ACC ATG-3' |
| 0.5 µl | Platinum Taq polymerase |
| 38.5 µl | H₂O |
| 50 µl | Total volume |

Run the following PCR program:

94° C.—3 minutes 40 cycles of:
- 94° C.—30 seconds
- 50° C.—30 seconds
- 72° C.—40 seconds 72° C.—5 minutes 4° C.—forever Purified PCR Product-QIAquick® PCR Purification Kit (Qiagen, Cat #28106)

a) Add 250 µl of Buffer PB to 50 µl PCR sample.

b) Place a QIAquick spin column in a provided 2 ml collection tube.

c) To bind DNA, apply the sample to the QIAquick column and centrifuge for 30-60 s.

d) Discard flow-through. Place the QIAquick column back into the same tube.

e) To wash, add 0.75 ml Buffer PE to the QIAquick column and centrifuge for 3060 s.

f) Discard flow-through and place the QIAquick column back in the same tube.

g) Centrifuge the column for an additional 1 min.

h) Place QIAquick column in a clean 1.5 ml microcentrifuge tube.

i) To elute DNA, add 50 µl Buffer EB (10 mM Tris-Cl, pH 8.5) or H2O to the center of the QIAquick membrane, let the column stand for 1 min, and then centrifuge the column for 1 min.

j) Measure O.D. of the PCR product and dilute to make 60 fg/µl stock.

3. Make 1 ml of 1 µM primer mix A stock by mixing 10 µl of 100 µM oligos stock (Table 2(a)) and add water to 1 ml. Mix well, then split to 100 µl aliquots.

4. Make 1 ml of 1 µM primer mix B stock by mixing 10 µl of 100 µM oligos stock (Table 2(b)) and add water to 1 ml. Mix well, then split to 100 µl aliquots.

Multiplex PCR

1. Nucleic Acid Extraction—MASTERPURE™ DNA purification kit (Epicentre, Cat #MC89010).

a) Add 100 µl of 1×PBS to 50 µl of Nasal Washes.

b) Add 150 µl 2×T & C lysis solution with 1 µl of proteinase K.

c) Incubate at 65° C. for 15 minutes, vortex every 5 minutes.

d) Incubate on ice or 4° C. for 3-5 minutes.

e) Add 150 µl MPC solution to the sample, vortex for 10 seconds.

f) Spin at maximum speed for 10 minutes.

g) Transfer the supernatant to a fresh 1.5 ml tube, then, add 500 µl isopropanol, mix well.

h) Spin at maximum speed at 4° C. for 10 minutes. Discard the supernatant, then wash with 80% alcohol twice.

i) Dry the pellet and resuspend in 8 µl nuclease free water.

2. Reverse Transcription with primer LN—Invitrogen Superscript III (Invitrogen, Cat. #18080-093)

```
NA from step 1          8 µl
primer LN (40 µM)       1 µl
5'-CGA TAC GAC GGG CGT ACT AGC GNN NNN NNN N-3'
10 mM dNTPs             1 µl
TIM (60 fg/µl)          1 µl
NAC1 (60 fg/µl)         1 µl Total volume           12 µl
```

Incubate at 65° C. for 5 minutes, then put on ice for >1 minute

Add the following reaction mix to the tube and mix gently by pipeting:

| | |
|---|---|
| 5X First-Strand buffer | 4 µl |
| 0.1 M DTT | 2 µl |
| RNaseOUT | 1 µl |
| SuperScript III | 1 µl |
| Total volume | 8 µl |

Run the following program on PCR machine:

25° C.—10 minutes
50° C.—50 minutes
85° C.—5 minutes

3. Split Multiplex PCR with primer L a. Reaction A:

```
10X PCR buffer              5 µl
50 mM MgCl2                 4 µl
50X dNTPs                   2 µl
primer L (100 µM)           1 µl
5'-CGA TAC GAC GGG CGT ACT AGC G-3'
Primer A mix (1 µM)         2 µl
5x Q-solution               5 µl
RT template (from step 2)  10 µl
Platinum taq                2 µl
Nuclease-free water        18 µl
UDG                         1 µl Total Volume               50 µl
``` b. Reaction B:

```
10X PCR buffer              5 µl
50 mM MgCl2                 4 µl
50X dNTPs                   2 µl
primer L (100 µM)           1 µl
5'-CGA TAC GAC GGG CGT ACT AGC G-3'
Primer B mix (1 µM)       2.5 µl
5x Q-solution               5 µl
RT template                10 µl
Platinum taq                2 µl
Nuclease-free water      17.5 µl
UDG                         1 µl Total Volume               50 µl
```

Run the following PCR program:

94° C.—3 minutes 5 cycles of:
94° C.—30 seconds
50° C.—90 seconds
72° C.—2 minutes 35 cycles of:
94° C.—30 seconds
64° C.—2 minutes 72° C.—5 minutes 4° C.—forever Array Preparation Tag IQ-EX PCR—1.0 kb Tag IQ-EX or 7.5 kb Tag IQ-EX 1.0 kb Tag IQ-EX PCR

| | |
|---|---|
| Forward primer (1 kb) | 3 µl |
| Reverse primer | 3 µl |
| Tag IQ-EX | 5 µl |
| MgCl$_2$ (50 mM) | 5 µl |
| dNTP (10 mM) | 2 µl |
| 10X PCR Buffer | 10 µl |
| Platinum Taq DNA polymerase | 1 µl |
| Water | 71 µl |
| Total volume | 100 µl |

94° C., 3'
30 cycles of 94° C., 30"; 68° C., 30"; 72° C., 40"
72° C., 10'

7.5 kb Tag IQ-EX PCR

| | |
|---|---|
| Forward primer (7.5 kb) | 3 µl |
| Reverse primer | 3 µl |
| Tag IQ-EX | 5 µl |
| dNTP (LA PCR kit) | 16 µl |
| 10X PCR Buffer (LA PCR kit) | 10 µl |
| TaKaRa Taq | 1 µl |
| Water | 62 µl |
| Total volume | 100 µl |

94° C., 3'
30 cycles of 94° C., 30"; 68° C., 7'30"
68° C., 10'

Purified PCR Products (Tag IQ-EX and Multiplex PCR)—QIAquick® PCR Purification Kit (Qiagen, Cat #28106)

a) Add 500 µl of Buffer PB to 100 µl PCR sample (combine reaction A and B).
b) Place a QIAquick spin column in a provided 2 ml collection tube.
c) To bind DNA, apply the sample to the QIAquick column and centrifuge for 30-60 s.
d) Discard flow-through. Place the QIAquick column back into the same tube.
e) To wash, add 0.75 ml Buffer PE to the QIAquick column and centrifuge for 30-60 s.
f) Discard flow-through and place the QIAquick column back in the same tube.
g) Centrifuge the column for an additional 1 min.
h) Place QIAquick column in a clean 1.5 ml microcentrifuge tube.
i) To elute DNA, add 40 µl Buffer EB (10 mM Tris-Cl, pH 8.5) or H2O to the center of the QIAquick membrane, let the column stand for 1 min, and then centrifuge the column for 1 min.
j) Measure O.D. of the PCR product.

Fragmentation and Labeling

1. Set up one tube per sample for fragmentation, add EB buffer to final volume 35 µl for each reaction. Treat Tag IQ-EX as one sample

| | | |
|---|---|---|
| Line 1 | Total µg of product to add to an array | 1.4 µg |
| Line 2 | Number of fragmentation reagent U required to fragment DNA | Line 1 × 0.15 = 0.21 U |

-continued

| | | |
|---|---|---|
| Line 3 | Activity of Fragmentation reagent (U/μl) | 3 U/μl |
| Line 4 | Volume of Fragmentation reagent required for each reaction (μl) | Line 2 ÷ line 3 = 0.07 μl |
| Line 5 | Volume of water required for each reaction (μl) | 3.3 − line 4 = 3.23 μl |

2. On ice prepare the fragmentation cocktail

| | |
|---|---|
| 10X fragmentation buffer | 4.3 μl |
| water | 3.23 μl |
| Fragmentation reagents | 0.07 μl |
| Total volume | 7.6 μl |

3. Chilled the fragmentation cocktail on ice, then added 7.6 μl to each DNA prepared from step 1 & 2.
4. Run the following program.
37° C., 5'
95° C., 10'
4° C., hold
5. Prepare the labeling cocktail (per reaction)

| | |
|---|---|
| Tdt buffer (5X) | 12 μl |
| GeneChip DNA labeling reagent (5 mM) | 2 μl |
| TdT (30 U/μl) | 3.4 μl |
| Total | 17.4 μl |

6. Add 17.4 μl of the labeling cocktail to one each of reactions and control fragmented PCR product.
7. Run the following program.
37° C., 30'
95° C., 5'
4° C., hold Hybridization
1. Turn on the hybridization oven set at 45° C., warm the chips to room temperature.
2. Prepare the pre-hybridization solution.

| | |
|---|---|
| 1% Tween-20 | 2 μl |
| 1 M Tris, pH 7.8 | 2 μl |
| Water | 196 μl |
| Total volume (per chip) | 200 μl |

3. Pre-hybridize the chips with pre-hybridization buffer at 45° C.
4. Assemble the hybridization master mix.

| | |
|---|---|
| Tag IQ-EX* (fragmented 0.26 μg) | 1.9 μl |
| 5 M TMAC | 132 μl |
| 1 M Tris, pH 7.8 | 2.2 μl |
| 1% Tween-20 | 2.2 μl |
| Herring sperm DNA (10 mg/ml) | 2.2 μl |
| Acetylated BSA | 2.2 μl |
| Control oligo B2 | 3.4 μl |
| Water | 13.9 μl |
| Final volume (per chip) | 160 μl |

*Use the following calculation to determine how much fragmented Tag IQ-EX for hybridization master mix.

Purified PCR product conc. (e.g. 100 ng/μl)×35 μl=3500 ng
Final volume after fragmentation and labeling is 60 μl
Final conc. of fragmented Tag IQ-EX=58.3 ng/μl
You will need 260/58.3=4.4658.3 μl
5. Add 160 μl to 60 μl labeled samples. Run the following program.
95° C., 5'
45° C., 5'
6. Remove the pre-hybridization buffer from the chip and fill with hybridization mix.
7. Hybridize overnight at 45° C., 60 rpm.

Washing and Staining
1. Prepare Washing buffer A & B

| Wash A | |
|---|---|
| 20X SSPE | 300 ml |
| 10% Tween-20 | 1 ml |
| Water | 699 ml |
| Wash B | |
| 20X SSPE | 30 ml |
| 10% Tween-20 | 1 ml |
| Water | 969 ml |

Filter through a 0.2 μm filter and stored capped at room temperature.

2. Prepare SAPE stain solution (each chip)

| | |
|---|---|
| 20X SSPE | 360 μl |
| 1% Tween-20 | 12 μl |
| 50 mg/ml acetylated BSA | 50 μl |
| SAPE | 12 μl |
| DI water | 766 μl |

Mix well and divide to two aliquots of 600 μl (stain 1 & stain 3)

3. Prepare Antibody solution (each chip)

| | |
|---|---|
| 20X SSPE | 180 μl |
| 1% Tween-20 | 6 μl |
| 50 mg/ml acetylated BSA | 25 μl |
| 10 mg/ml Normal goat IgG | 6 μl |
| 0.5 mg/ml biotinylated antibody | 3.6 μl |
| DI water | 379.4 μl |
| Final volume | 600 μl |

4. Run wash protocol-DNAARRAY WS4.

Unlike traditional methods, the optimized RPM v.1 assay may not only identify pathogens, but may also provide sequence information, allowing a large number of pathogens to be detected and phylogenetically categorized in the same assay. The sequence information demonstrated the capability of RPM v.1 for identifying a broad range of variants (e.g. HAdVs) which is a powerful tool for genetic variation analysis of the circulating and emerging viruses (i.e. influenza). This is also useful in tracking the movement of known variants. This utility was clearly demonstrated in the Influenza A positive clinical samples showing the lineages change from A/A/Panama/2007/99-like strains (prior 2003 influenza season) to A/Fujian/411/2002-like strain in 2003-2004 influenza season, then to A/California/7/2004-like strains in 2004-2005 influenza season. Only one M gene (H1N1) sequence, which is relatively conserved among influenza A viruses, was tiled on the RPM v.1. But the M gene ProSeq was still able to detect homologous regions of disparate subtypes, allowing correct differentiation (Table 10). This M gene ProSeq would theoretically allow detection of any other type of influenza virus for which antigenic HA and NA sequences were not tiled on the array.

This study demonstrates that this system may exhibit excellent clinical sensitivity and specificity, the ability to resolve complex co-infections without a loss of sensitivity, and the sensitivity is similar to all 26 targeted pathogens and potential biowarfare agents. In contrast to both culture and PCR assays, this assay platform showed comparable detection sensitivity and specificity for both HAdV and influenza A virus (Table 7). The data supports the feasibility of using the RPM v.1 system as a diagnostic tool to correctly identify and type clinically relevant adenovirus and influenza A virus strains in direct (uncultured) clinical specimens, in a manner that correlates well with conventional detection methods.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A method comprising:

extracting nucleic acids from a clinical sample obtained from an organism to produce a target sample containing background DNA of the organism and suspected of containing one or more pathogen nucleic acids from a predefined set of pathogens;

adding to the target sample a plurality of PCR primers corresponding to genes found in the predefined set of pathogens;

wherein the PCR primers include at least 30 different primer pairs;

wherein the primers include at least one primer pair for each pathogen;

wherein the primers comprise a tail sequence that is not homologous to the DNA of any of the predefined set of pathogens or to the DNA of the species of the organism; and performing a polymerase chain reaction on the combined target sample and PCR primers to amplify a subset of the nucleic acids that correspond to the genes to produce an amplified sample;

wherein the concentration of at least one primer in the polymerase chain reaction is no more than 50 nM.

2. The method of claim 1, wherein no primer in the polymerase chain reaction is at a concentration greater than about 100 nM.

3. The method of claim 1, wherein the tail sequence is

CGATACGACGGGCGTACTAGCG      (SEQ ID NO.1).

4. The method of claim 1, wherein the tail sequence is

CGATACGACGGGCGTACTAGCGNNNNNNNNNN      (SEQ ID NO.2).

5. The method of claim 1, wherein the clinical sample comprises a nasal wash, a throat swab, sputum, blood, or an environmental sample.

6. The method of claim 1, wherein the organism is human.

7. The method of claim 1, wherein the pathogens are respiratory pathogens.

8. The method of claim 1, wherein the pathogens are enteric pathogens or biothreat agents.

9. The method of claim 1, wherein the amplified nucleic acids include a sequence of less than 200 nucleotides and a sequence of more than 2000 nucleotides.

10. The method of claim 1, wherein the tail sequence reduces the formation of primer-dimers.

11. The method of claim 1, wherein the PCR primers include at least 50 different primer pairs.

12. The method of claim 1,
wherein adding the plurality PCR primers and performing the polymerase chain reaction are each performed on a plurality of aliquots of the target sample;
wherein a different plurality PCR primers is used for each aliquot; and
wherein the aliquots are combined after the PCR reactions.

13. The method of claim 1, further comprising:
contacting the amplified sample to a microarray comprising a plurality of nucleic acid sequences that are complementary to at least portions of the amplified nucleic acids; and
allowing the amplified nucleic acids to hybridize to complementary nucleic acids.

14. The method of claim 13, wherein the complementary nucleic acids are from 25- to 29-mers.

15. The method of claim 13, wherein the complementary nucleic acids include a perfect match probes to at least one of the amplified nucleic acids and three different single nucleotide polymorphisms of the center position of each perfect match probe.

16. The method of claim 13, further comprising:
detecting which amplified nucleic acids are hybridized to the complementary nucleic acids.

17. The method of claim 16, further comprising:
identifying the pathogen based on which amplified nucleic acids are detected.

18. The method of claim 17, wherein the identification is based upon pattern recognition.

19. The method of claim 17, wherein the identification is based on sequencing of the amplified nucleic acids.

20. The method of claim 17, wherein the identification includes the strain of the pathogen.

21. The method of claim 16, wherein the detection of the hybridized amplified nucleic acids occurs when an optical signal corresponding to the hybridized amplified nucleic acid has an intensity exceeding a predetermined signal-to-noise ratio.

22. The method of claim 1, wherein the predefined set of pathogens comprises at least one bacterium.

23. The method of claim 1, wherein the concentration of each primer in the polymerase chain reaction is no more than 50 nM.

24. A method comprising:
providing a biological sample suspected of containing one or more pathogen nucleic acids from a predefined set of pathogens;
adding to the biological sample a plurality of PCR primers corresponding to genes found in the predefined set of pathogens;
wherein the primers include at least one primer pair for each pathogen;
wherein the primers comprise a tail sequence that is not homologous to the DNA of any of the predefined set of pathogens or to any background DNA in the sample;
wherein the tail sequence is

```
CGATACGACGGGCGTACTAGCG or            (SEQ ID NO.1)
CGATACGACGGGCGTACTAGCGNNNNNNNNNN; and (SEQ ID NO.2)
``` performing a polymerase chain reaction on the combined biological sample and PCR primers to amplify a subset of the nucleic acids that correspond to the genes;
wherein the concentration of at least one primer in the polymerase chain reaction is no more than about 100 nM.

* * * * *